United States Patent [19]

Taniguchi et al.

[11] Patent Number: 4,571,397
[45] Date of Patent: Feb. 18, 1986

[54] PYRIDAZINONE DERIVATIVES, PREPARATION THEREOF, AND AGRICULTURAL AND HORTICULTURAL FUNGICIDAL, INSECTICIDAL, ACARICIDAL, NEMATICIDAL COMPOSITIONS CONTAINING SAID DERIVATIVES

[75] Inventors: Masakazu Taniguchi; Masatoshi Baba, both of Funabashi; Yoshinori Ochiai, Shiraoka; Masayoshi Hirose, Shiraoka; Kiminori Hirata, Shiraoka, all of Japan

[73] Assignee: Nissan Chemical Industries, Tokyo, Japan

[21] Appl. No.: 467,259

[22] Filed: Feb. 17, 1983

[30] Foreign Application Priority Data

Mar. 5, 1982 [JP] Japan .................................. 57-34991
Aug. 27, 1982 [JP] Japan ................................ 57-149446
Oct. 18, 1982 [JP] Japan ................................ 57-182499
Nov. 25, 1982 [JP] Japan ................................ 57-206438

[51] Int. Cl.$^4$ .................... C07D 237/06; A61K 31/50
[52] U.S. Cl. .................................. 514/252; 544/238; 544/239; 71/92
[58] Field of Search ...................... 544/239, 231, 238; 71/92; 514/252

[56] References Cited

U.S. PATENT DOCUMENTS 3,652,257 3/1972 Jojima et al. ...................... 544/239

FOREIGN PATENT DOCUMENTS 2706700 8/1978 Fed. Rep. of Germany .
2732101 1/1979 Fed. Rep. of Germany .
43-11902 5/1968 Japan .
12879 4/1978 Japan .
111472 7/1980 Japan .
113767 1/1981 Japan .
917849 2/1963 United Kingdom .

OTHER PUBLICATIONS

Pesticide Sci., vol. 4, pp. 775-783 (1973).
Pesticide Sci., vol. 7, pp. 97-106 (1976).
Chem. Abstracts, vol. 90, 168636u (1979).
Chem. Abstracts, vol. 92, 41867f (1980).
Chem. Abstracts, vol. 93, 132432x (1980).
Chem. Abstracts, vol. 94, 84044u (1981).

Primary Examiner—Nicholas S. Rizzo
Attorney, Agent, or Firm—Quaintance, Murphy & Presta

[57] ABSTRACT

Novel 5-substituted -3(2H)-pyridazinone derivatives and preparation thereof are provided.

The derivatives have the formula:

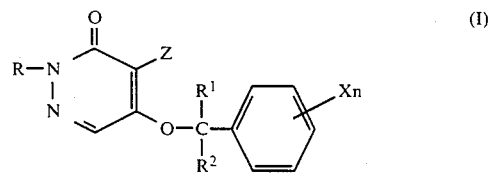

wherein, R denotes an alkyl, $R^1$ and $R^2$ denote each independently hydrogen or a lower alkyl, X denotes hydrogen, a lower alkyl, a halogen, a lower alkoxy, a lower haloalkyl, a lower haloalkoxy, a cycloalkyl, trimethylsilyl ($-Si(CH_3)_3$),

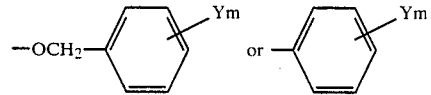

(wherein Y denotes hydrogen, a halogen, a lower alkyl, a lower alkoxy, a lower haloalkyl, a lower haloalkoxy or a cycloalkyl, and m is an integer of 1 to 5), n is an integer of 1 to 5, and Z denotes a halogen; said X being the same or different when n is 2 or more, and the alkyls and the alkyl moieties contained in the groups being straight or branched.

33 Claims, No Drawings

PYRIDAZINONE DERIVATIVES, PREPARATION THEREOF, AND AGRICULTURAL AND HORTICULTURAL FUNGICIDAL, INSECTICIDAL, ACARICIDAL, NEMATICIDAL COMPOSITIONS CONTAINING SAID DERIVATIVES

BACKGROUND OF THE INVENTION (1) Field of the Invention:

This invention relates to novel 5-substituted-3(2H)-pyridazinone derivatives, preparation thereof, and agricultural and horticultural fungicidal, insecticidal, acaricidal, nematicidal compositions containing said derivatives.

(2) Description of the Prior Art:

Hitherto, a pyridaphenthion (known under the trade name Ofunack) of the following formula IV has been put into practice as an active ingredient of an insecticide containing a 3(2H)-pyridazinone ring:

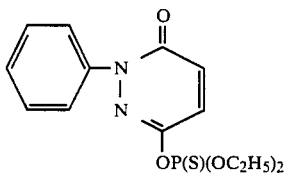
(IV)

On the other hand, it is known that the compounds of the formula V and the compounds of the formula VI exhibit insecticidal and acaricidal action [refer to West Germany Pat. No. 2,732,101 as to the compounds (V); and Pesticide Sci. Vol 4, p. 775 (1973) and Vol. 7, p. 97 and 107 (1976), and Chem. Abstr. Vol. 90, 168636 u (1979), Vol. 92, 41867f (1980), Vol. 93, 132432x (1980) and Vol. 94, 84044u (1981) as to the compounds (VI)]:

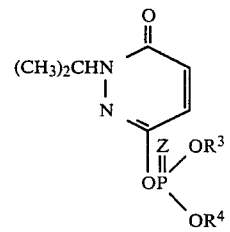
(V)

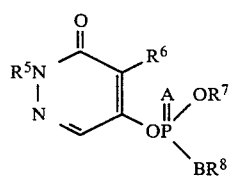
(VI)

wherein, $R^3$ and $R^4$ are each a lower alkyl, Z is oxygen or sulfur atom, $R^5$, $R^7$ and $R^8$ are each an alkyl, $R^6$ is a halogen or an alkoxy, and A and B are each oxygen or sulfur.

All the compounds of the formulae IV, V and VI, however, are those classified as organic phosphorous insecticides and, therefore, apparently different from and not related at all to the compounds according to the present invention.

It is also known that the compounds of formula VII and those of the formula VIII are useful for Sheath blight (*Pellicularia sasakii*) (refer to, for example, Japanese Laid-Open Patent Publication No. 12879/78; and Japanese Laid-Open Patent Publications No. 111472/80 and 113767/81, respectively):

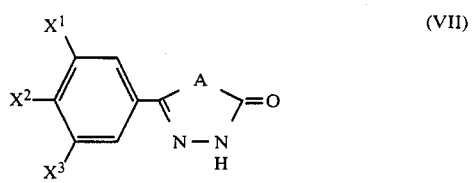
(VII)

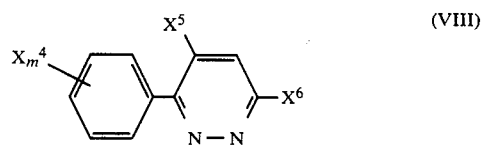
(VIII)

wherein A denotes $-CH_2CH_2-$ or $-CH=CH-$, $X^1$, $X^2$ and $X^3$ denotes, for example $X^1=X^3=Cl$, $X^2=CH_3$ and $X^4$ is hydrogen, halogen, alkyl, etc. $X^5$ is chlorine, $X^6$ is hydrogen or halogen.

Also the compounds (VII) and (VIII) are completely different from those of the present invention in that the former have a phenyl ring (which may be substituted) at 6-position but do not have a substituent at 2-position.

Thus present inventors have synthesized many kinds of 3(2H)-pyridazinone derivatives and searched on pesticidal activities thereof in order to develop novel and useful pesticides, and have found that such 3(2H)-pyridazinones that have specified substituents at 5-position exhibit excellent fungicidal, insecticidal, acaricidal, nematicidal activities to complete the invention.

SUMMARY OF THE INVENTION

An object of this invention is to provide novel pesticidal 3(2H)-pyridazinone derivatives which have excellent residual activity and low toxicity to mammals.

Another object of this invention is to provide novel 3(2H)-pyridazinone derivatives which have insecticidal, acaricidal fungicidal and nematicidal activities.

Still another object of this invention is to provide a process for preparing such 3(2H)-pyridazinone derivatives.

Further object of this invention is to provide fungicidal, insecticidal, acaricidal, nematicidal compositions containing a 3(2H)-pyridazinone derivative as an active ingredient.

Still further object of the present invention is to provide a method for fungicidal, insecticidal, acaricidal, nematicidal treatment with 3(2H)-pyridazinone derivatives.

The 3(2H)-pyridazinone derivative according to the invention have the general formula (I):

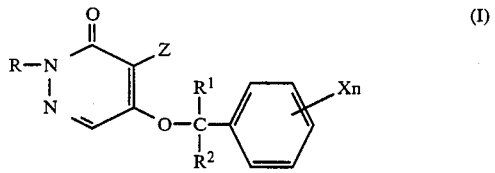
(I)

wherein, R denotes an alkyl, $R^1$ and $R^2$ denote each independently hydrogen or a lower alkyl, X denotes hydrogen, a lower alkyl, a halogen, a lower alkoxy, a lower haloalkyl, a lower haloalkoxy, a cycloalkyl, trimethylsilyl ($-Si(CH_3)_3$),

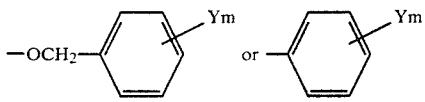

(wherein Y denotes hydrogen, a halogen, a lower alkyl, a lower alkoxy, a lower haloalkyl, a lower haloalkoxy or a cycloalkyl, and m is an integer of 1 to 5, n is an integer of 1 to 5, and Z denotes a halogen; said X being the same or different when n is 2 or more, and the alkyls and the alkyl moieties contained in the groups being straight or branched.

These and other objects and many of the attendant advantages of this invention will be readily appreciated as the same becomes better understood by reference to the following detailed description.

DESCRIPTION OF THE PREFERRED EMBODIMENTS

The "lower alkyl" including the lower alkyl moieties contained in the groups such as "lower alkoxy", "lower haloalkyl" and "lower haloalkoxy" are usually a straight or branched alkyl of 1 to 6 carbon atoms, preferably of 1 to 4 carbon atoms such as methyl, ethyl, n-propyl, i-propyl, n-butyl, sec.-butyl or tert.-butyl.

The term "halogen" and halogens contained in the groups such as "haloalkyl" and "haloalkoxy" mean fluorine, chlorine, bromine, iodine atom or a mixture thereof.

The "cycloalkyl" as a substituent X or Y preferably has 5 to 6 carbon atoms.

R is preferably a straight or branched alkyl of 1 to 6 carbon atoms, such as methyl, ethyl, n-propyl, i-propyl, n-butyl, sec.-butyl, tert.-butyl, n-amyl or n-hexyl, and most preferably tert.-butyl.

$R^1$ and $R^2$ are each preferably hydrogen or a straight or branched alkyl of 1 to 4 carbon atoms, such as methyl, ethyl, n-propyl, i-propyl, n-butyl, sec.-butyl or tert.-butyl, and more preferably hydrogen, methyl or ethyl.

X is preferably hydrogen, methyl, i-propyl, tert.-butyl, halogen, cyclohexyl, phenyl, benzyloxy, more preferably tert.-butyl, chlorine, fluorine, cyclohexyl, phenyl, benzyloxy, trimethylsilyl, and most preferably tert.-butyl, cyclohexyl, phenyl, or benzyloxy.

Z is preferably chlorine or bromine, more preferably chlorine.

n is preferably an integer of 1 to 3, more preferably 1 or 2, and most preferably 1.

The first group of the compounds (I) is represented by the formula IA:

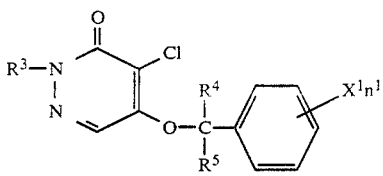

wherein, $R^3$ denotes an alkyl; $R^4$ denotes a lower alkyl; $R^5$ denotes hydrogen or a lower alkyl; $X^1$ denotes hydrogen, a lower alkyl, a lower alkoxy, a lower haloalkyl, a lower haloalkoxy, a halogen or a cycloalkyl, and $n^1$ is an integer of 1 to 5; said $X^1$ being the same or different when n is 2 to 5, and the alkyls and the alkyl moieties contained in the groups being straight or branched.

Among the compounds of the formula IA, i.e. compounds (IA), preferred are those wherein $R^3$ is an alkyl of 1 to 6 carbon atoms, particularly an alkyl of 1 to 4 carbon atoms such as methyl, ethyl, n-propyl, i-propyl, n-butyl and tert.-butyl; $R^4$ is a lower alkyl of 1 to 4 carbon atoms, particularly methyl or ethyl; $R^5$ is hydrogen or a lower alkyl of 1 to 4 carbon atoms, particularly hydrogen, methyl or ethyl and more particularly hydrogen; $X^1$ is hydrogen, a lower alkyl of 1 to 4 carbon atoms, fluorine, chlorine, bromine, a lower alkoxy of 1 or 2 carbon atom(s), a lower haloalkyl of one carbon atom, a lower haloalkoxy of 1 or 2 carbon atom(s) or a cycloalkyl of 5 or 6 carbon atoms, particularly hydrogen, fluorine, chlorine, bromine, methyl, ethyl, n-propyl, i-propyl, tert.-butyl, cyclopentyl or cyclohexyl; and $n^1$ is 1 or 2, particularly 1. Substituent $X^1$ is preferably located at 3- or 4-position, more preferably at 4-position.

The compounds (IA) are illustrated in Table 1.

TABLE 1

Compounds of the formula IA:

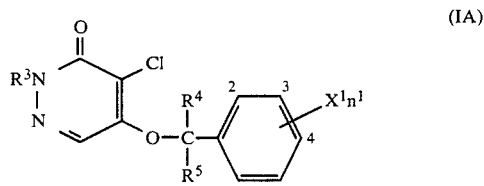

| Compound No. | $R^3$ | $R^4$ | $R^5$ | $X^1 n^1$ |
|---|---|---|---|---|
| 1.1 | CH$_3$ | CH$_3$ | H | H |
| 1.2 | CH$_3$ | CH$_3$ | H | 4-Cl |
| 1.3 | CH$_3$ | CH$_3$ | H | 4-i-C$_3$H$_7$ |
| 1.4 | CH$_3$ | CH$_3$ | H | 2-OCH$_3$ |
| 1.5 | CH$_3$ | C$_2$H$_5$ | H | 3,4-Cl$_2$ |
| 1.6 | CH$_3$ | n-C$_3$H$_7$ | H | 3-OC$_2$H$_5$ |
| 1.7 | CH$_3$ | CH$_3$ | CH$_3$ | H |
| 1.8 | C$_2$H$_5$ | CH$_3$ | H | H |
| 1.9 | C$_2$H$_5$ | CH$_3$ | H | 3-Cl |
| 1.10 | C$_2$H$_5$ | CH$_3$ | H | 4-F |
| 1.11 | C$_2$H$_5$ | CH$_3$ | H | 4-Cl |
| 1.12 | C$_2$H$_5$ | CH$_3$ | H | 4-Br |
| 1.13 | C$_2$H$_5$ | CH$_3$ | H | 3-CH$_3$ |
| 1.14 | C$_2$H$_5$ | CH$_3$ | H | 3-CF$_3$ |
| 1.15 | C$_2$H$_5$ | CH$_3$ | H | 4-CH$_3$ |
| 1.16 | C$_2$H$_5$ | CH$_3$ | H | 4-i-C$_3$H$_7$ |
| 1.17 | C$_2$H$_5$ | CH$_3$ | H | 4-t-C$_4$H$_9$ |
| 1.18 | C$_2$H$_5$ | CH$_3$ | H | 4-cyclo-C$_5$H$_9$ |
| 1.19 | C$_2$H$_5$ | CH$_3$ | H | 4-cyclo-C$_6$H$_{11}$ |
| 1.20 | C$_2$H$_5$ | C$_2$H$_5$ | H | H |
| 1.21 | C$_2$H$_5$ | C$_2$H$_5$ | H | 4-Cl |
| 1.22 | C$_2$H$_5$ | C$_2$H$_5$ | H | 4-CH$_3$ |
| 1.23 | C$_2$H$_5$ | C$_2$H$_5$ | H | 4-t-C$_4$H$_9$ |
| 1.24 | C$_2$H$_5$ | C$_2$H$_5$ | H | 4-cyclo-C$_6$H$_{11}$ |
| 1.25 | C$_2$H$_5$ | CH$_3$ | CH$_3$ | H |
| 1.26 | C$_2$H$_5$ | C$_2$H$_5$ | C$_2$H$_5$ | H |
| 1.27 | n-C$_3$H$_7$ | CH$_3$ | H | 4-F |
| 1.28 | n-C$_3$H$_7$ | CH$_3$ | H | 2-CH$_3$ |
| 1.29 | n-C$_3$H$_7$ | CH$_3$ | H | 4-t-C$_4$H$_9$ |
| 1.30 | n-C$_3$H$_7$ | CH$_3$ | H | 4-cyclo-C$_6$H$_{11}$ |
| 1.31 | n-C$_3$H$_7$ | CH$_3$ | H | 4-OCF$_3$ |
| 1.32 | n-C$_3$H$_7$ | CH$_3$ | H | 3-OCH$_2$CF$_3$ |
| 1.33 | n-C$_3$H$_7$ | C$_2$H$_5$ | H | H |
| 1.34 | n-C$_3$H$_7$ | n-C$_3$H$_7$ | H | 4-Cl |
| 1.35 | n-C$_3$H$_7$ | C$_2$H$_5$ | CH$_3$ | H |
| 1.36 | n-C$_3$H$_7$ | i-C$_3$H$_7$ | C$_2$H$_5$ | H |
| 1.37 | i-C$_3$H$_7$ | CH$_3$ | H | H |
| 1.38 | i-C$_3$H$_7$ | CH$_3$ | H | 4-t-C$_4$H$_9$ |
| 1.39 | i-C$_3$H$_7$ | CH$_3$ | H | 4-cyclo-C$_6$H$_{11}$ |
| 1.40 | i-C$_3$H$_7$ | CH$_3$ | H | 4-OCH$_3$ |
| 1.41 | i-C$_3$H$_7$ | C$_2$H$_5$ | H | 4-OC$_2$H$_5$ |
| 1.42 | i-C$_3$H$_7$ | n-C$_4$H$_9$ | H | H |

TABLE 1-continued

Compounds of the formula IA:

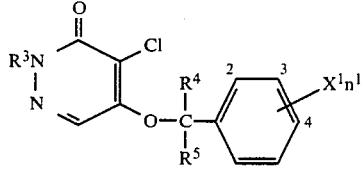

(IA)

| Compound No. | $R^3$ | $R^4$ | $R^5$ | $X^1n^1$ |
|---|---|---|---|---|
| 1.43 | i-$C_3H_7$ | $CH_3$ | $CH_3$ | 2-Cl |
| 1.44 | i-$C_3H_7$ | $C_2H_5$ | $CH_3$ | 4-$CH_3$ |
| 1.45 | n-$C_4H_9$ | $CH_3$ | H | 3-Cl |
| 1.46 | n-$C_4H_9$ | $CH_3$ | H | 4-t-$C_4H_9$ |
| 1.47 | n-$C_4H_9$ | $CH_3$ | H | 4-cyclo-$C_6H_{11}$ |
| 1.48 | n-$C_4H_9$ | $CH_3$ | H | 3-$CF_3$ |
| 1.49 | n-$C_4H_9$ | $CH_3$ | $CH_3$ | 4-Br |
| 1.50 | n-$C_4H_9$ | $CH_3$ | $CH_3$ | 4-t-$C_4H_9$ |
| 1.51 | n-$C_4H_9$ | $CH_3$ | $CH_3$ | 4-$CF_3$ |
| 1.52 | n-$C_4H_9$ | $C_2H_5$ | $CH_3$ | 4-Cl |
| 1.53 | i-$C_4H_9$ | $CH_3$ | H | H |
| 1.54 | i-$C_4H_9$ | $CH_3$ | H | 4-F |
| 1.55 | i-$C_4H_9$ | $CH_3$ | H | 3-Cl |
| 1.56 | i-$C_4H_9$ | $CH_3$ | H | 3-$CH_3$ |
| 1.57 | i-$C_4H_9$ | $CH_3$ | H | 4-cyclo-$C_5H_9$ |
| 1.58 | i-$C_4H_9$ | $CH_3$ | H | 3-$CF_3$ |
| 1.59 | i-$C_4H_9$ | $CH_3$ | H | 4-$OCH_2CF_3$ |
| 1.60 | i-$C_4H_9$ | $C_2H_5$ | H | 4-t-$C_4H_9$ |
| 1.61 | i-$C_4H_9$ | $CH_3$ | $CH_3$ | 4-F |
| 1.62 | i-$C_4H_9$ | n-$C_3H_7$ | $CH_3$ | H |
| 1.63 | i-$C_4H_9$ | n-$C_4H_9$ | $CH_3$ | H |
| 1.64 | sec-$C_4H_9$ | $CH_3$ | H | 4-Br |
| 1.65 | sec-$C_4H_9$ | $CH_3$ | H | 2-$CF_3$ |
| 1.66 | sec-$C_4H_9$ | $CH_3$ | H | 4-i-$C_3H_7$ |
| 1.67 | sec-$C_4H_9$ | $CH_3$ | H | 4-cyclo-$C_5H_9$ |
| 1.68 | sec-$C_4H_9$ | $CH_3$ | H | 2,4,6-$(CH_3)_3$ |
| 1.69 | sec-$C_4H_9$ | $CH_3$ | $CH_3$ | H |
| 1.70 | sec-$C_4H_9$ | $C_2H_5$ | $CH_3$ | H |
| 1.71 | sec-$C_4H_9$ | $C_2H_5$ | $C_2H_5$ | 4-t-$C_4H_9$ |
| 1.72 | t-$C_4H_9$ | $CH_3$ | H | H |
| 1.73 | t-$C_4H_9$ | $CH_3$ | H | 4-F |
| 1.74 | t-$C_4H_9$ | $CH_3$ | H | 3-Cl |
| 1.75 | t-$C_4H_9$ | $CH_3$ | H | 4-Cl |
| 1.76 | t-$C_4H_9$ | $CH_3$ | H | 4-Br |
| 1.77 | t-$C_4H_9$ | $CH_3$ | H | 3-$CH_3$ |
| 1.78 | t-$C_4H_9$ | $CH_3$ | H | 4-$CH_3$ |
| 1.79 | t-$C_4H_9$ | $CH_3$ | H | 4-i-$C_3H_7$ |
| 1.80 | t-$C_4H_9$ | $CH_3$ | H | 4-t-$C_4H_9$ |
| 1.81 | t-$C_4H_9$ | $CH_3$ | H | 4-cyclo-$C_6H_{11}$ |
| 1.82 | t-$C_4H_9$ | $CH_3$ | H | 2-$OCHF_2$ |
| 1.83 | t-$C_4H_9$ | $CH_3$ | H | 4-$OCH_2CF_3$ |
| 1.84 | t-$C_4H_9$ | $C_2H_5$ | H | H |
| 1.85 | t-$C_4H_9$ | $C_2H_5$ | H | 4-Cl |
| 1.86 | t-$C_4H_9$ | $C_2H_5$ | H | 4-$CH_3$ |
| 1.87 | t-$C_4H_9$ | $C_2H_5$ | H | 4-t-$C_4H_9$ |
| 1.88 | t-$C_4H_9$ | $C_2H_5$ | H | 4-cyclo-$C_6H_{11}$ |
| 1.89 | t-$C_4H_9$ | $C_2H_5$ | $CH_3$ | 4-Cl |
| 1.90 | t-$C_4H_9$ | $C_2H_5$ | $C_2H_5$ | 4-Br |
| 1.91 | i-$C_5H_{11}$ | $CH_3$ | H | H |
| 1.92 | i-$C_5H_{11}$ | $CH_3$ | H | 4-F |
| 1.93 | i-$C_5H_{11}$ | $CH_3$ | H | 2-$OCF_3$ |
| 1.94 | i-$C_5H_{11}$ | n-$C_4H_9$ | H | 4-Cl |
| 1.95 | i-$C_5H_{11}$ | $CH_3$ | $CH_3$ | 4-$CH_3$ |
| 1.96 | i-$C_5H_{11}$ | $C_2H_5$ | $C_2H_5$ | 4-Cl |
| 1.97 | n-$C_6H_{13}$ | $CH_3$ | H | H |
| 1.98 | n-$C_6H_{13}$ | $CH_3$ | H | 3-Cl |
| 1.99 | n-$C_6H_{13}$ | $CH_3$ | H | 4-i-$C_3H_7$ |
| 1.100 | n-$C_6H_{13}$ | $CH_3$ | H | 4-cyclo-$C_6H_{11}$ |
| 1.101 | n-$C_6H_{13}$ | $C_2H_5$ | H | H |
| 1.102 | n-$C_6H_{13}$ | $CH_3$ | $CH_3$ | 4-F |
| 1.103 | n-$C_6H_{13}$ | $C_2H_5$ | $CH_3$ | 4-Br |

The second group of the compounds (I) is represented by the formula IB:

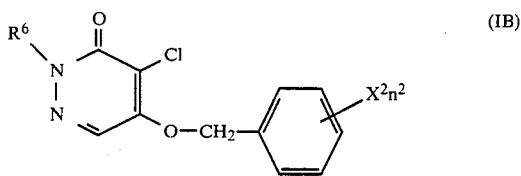

(IB)

wherein, $R^6$ denotes an alkyl having 1 to 6 carbon atoms; $X^2$ denotes hydrogen, a halogen, a lower alkyl, a lower alkoxy or a lower haloalkoxy; and $n^2$ is an integer of 1 to 3; said $X^2$ being the same or different when $n^2$ is 2 or 3 and the alkyls and the alkyl moieties contained in the groups being straight or branched.

Among the compounds (IB), preferred are those wherein $R^6$ is methyl, ethyl, n-propyl, i-propyl, n-butyl, tert.-butyl, n-amyl or n-hexyl, particularly methyl, ethyl, n-propyl, i-propyl, n-butyl, tert.-butyl or n-hexyl; $X^2$ is hydrogen, fluorine, chlorine, bromine, methyl, ethyl, i-propyl, tert.-butyl, methoxy, difluoromethoxy, trifluoromethoxy or —$OCF_2CHF_2$, particularly hydrogen, chlorine, fluorine, bromine, methyl, i-propyl, tert.-butyl or methoxy; and $n^2$ is an integer of 1 to 3, particularly 1 or 2.

The compounds (B) are illustrated in Table 2.

TABLE 2

Compounds of the formula IB:

| Compound No. | $R^6$ | $X^2n^2$ |
|---|---|---|
| 2.1 | $CH_3$ | H |
| 2.2 | $CH_3$ | 3-Cl |
| 2.3 | $CH_3$ | 4-Cl |
| 2.4 | $CH_3$ | 3-$CH_3$ |
| 2.5 | $CH_3$ | 4-$CH_3$ |
| 2.6 | $CH_3$ | 4-$CH(CH_3)_2$ |
| 2.7 | $CH_3$ | 4-$C(CH_3)_3$ |
| 2.8 | $CH_3$ | 4-F |
| 2.9 | $CH_3$ | 2,4,6-$(CH_3)_3$ |
| 2.10 | $CH_3$ | 4-$OCH_3$ |
| 2.11 | $CH_3$ | 2,4-$Cl_2$ |
| 2.12 | $CH_3$ | 3,4-$Cl_2$ |
| 2.13 | $CH_3$ | 2-Cl, 4-$CH_3$ |
| 2.14 | $C_2H_5$ | H |
| 2.15 | $C_2H_5$ | 3-Cl |
| 2.16 | $C_2H_5$ | 4-Cl |
| 2.17 | $C_2H_5$ | 3-$CH_3$ |
| 2.18 | $C_2H_5$ | 4-$CH_3$ |
| 2.19 | $C_2H_5$ | 4-$CH(CH_3)_2$ |
| 2.20 | $C_2H_5$ | 4-$C(CH_3)_3$ |
| 2.21 | $C_2H_5$ | 4-F |
| 2.22 | $C_2H_5$ | 4-Br |
| 2.23 | $C_2H_5$ | 4-$OCH_3$ |
| 2.24 | $C_2H_5$ | 2,4-$Cl_2$ |
| 2.25 | $C_2H_5$ | 3,4-$Cl_2$ |
| 2.26 | $C_2H_5$ | 4-$OCHF_2$ |
| 2.27 | n-$C_3H_7$ | H |
| 2.28 | n-$C_3H_7$ | 3-Cl |
| 2.29 | n-$C_3H_7$ | 4-Cl |
| 2.30 | n-$C_3H_7$ | 3-$CH_3$ |
| 2.31 | n-$C_3H_7$ | 4-$CH_3$ |
| 2.32 | n-$C_3H_7$ | 4-$CH(CH_3)_2$ |
| 2.33 | n-$C_3H_7$ | 4-$C(CH_3)_3$ |
| 2.34 | n-$C_3H_7$ | 4-F |
| 2.35 | n-$C_3H_7$ | 4-Br |
| 2.36 | n-$C_3H_7$ | 4-$OCH_3$ |
| 2.37 | n-$C_3H_7$ | 2-Cl, 4-$CH(CH_3)_2$ |
| 2.38 | n-$C_3H_7$ | 4-$OCF_3$ |

TABLE 2-continued

Compounds of the formula IB:

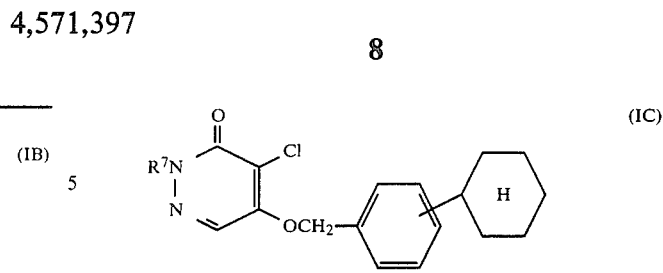

(IB)

| Compound No. | $R^6$ | $X^2n^2$ |
|---|---|---|
| 2.39 | n-$C_3H_7$ | 3-OCHF$_2$ |
| 2.40 | i-$C_3H_7$ | H |
| 2.41 | i-$C_3H_7$ | 3-Cl |
| 2.42 | i-$C_3H_7$ | 4-Cl |
| 2.43 | i-$C_3H_7$ | 3-CH$_3$ |
| 2.44 | i-$C_3H_7$ | 4-CH$_3$ |
| 2.45 | i-$C_3H_7$ | 4-CH(CH$_3$)$_2$ |
| 2.46 | i-$C_3H_7$ | 4-C(CH$_3$)$_3$ |
| 2.47 | i-$C_3H_7$ | 4-F |
| 2.48 | i-$C_3H_7$ | 4-Br |
| 2.49 | i-$C_3H_7$ | 4-CH$_3$O |
| 2.50 | i-$C_3H_7$ | 2,4-Cl$_2$ |
| 2.51 | i-$C_3H_7$ | 3,4-Cl$_2$ |
| 2.52 | i-$C_3H_7$ | 4-OCF$_2$CHF$_2$ |
| 2.53 | n-$C_4H_9$ | H |
| 2.54 | n-$C_4H_9$ | 2,4-(CH$_3$)$_2$ |
| 2.55 | n-$C_4H_9$ | 4-Cl |
| 2.56 | n-$C_4H_9$ | 3-CH$_3$ |
| 2.57 | n-$C_4H_9$ | 4-CH$_3$ |
| 2.58 | n-$C_4H_9$ | 4-CH(CH$_3$)$_2$ |
| 2.59 | n-$C_4H_9$ | 4-C(CH$_3$)$_3$ |
| 2.60 | n-$C_4H_9$ | 4-F |
| 2.61 | n-$C_4H_9$ | 4-Br |
| 2.62 | n-$C_4H_9$ | 4-OCH$_3$ |
| 2.63 | n-$C_4H_9$ | 2,4-Cl$_2$ |
| 2.64 | n-$C_4H_9$ | 2-Cl, 4-C(CH$_3$)$_3$ |
| 2.65 | n-$C_4H_9$ | 2,4,6-(CH$_3$)$_3$ |
| 2.66 | t-$C_4H_9$ | H |
| 2.67 | t-$C_4H_9$ | 4-CH$_2$CH$_3$ |
| 2.68 | t-$C_4H_9$ | 4-Cl |
| 2.69 | t-$C_4H_9$ | 3-CH$_3$ |
| 2.70 | t-$C_4H_9$ | 4-CH$_3$ |
| 2.71 | t-$C_4H_9$ | 4-CH(CH$_3$)$_2$ |
| 2.72 | t-$C_4H_9$ | 4-C(CH$_3$)$_3$ |
| 2.73 | t-$C_4H_9$ | 4-F |
| 2.74 | t-$C_4H_9$ | 4-Br |
| 2.75 | t-$C_4H_9$ | 4-OCH$_3$ |
| 2.76 | t-$C_4H_9$ | 2,4-Cl$_2$ |
| 2.77 | t-$C_4H_9$ | 3,4-Cl$_2$ |
| 2.78 | t-$C_4H_9$ | 3,4-(CH$_3$)$_2$ |
| 2.79 | n-$C_5H_{11}$ | H |
| 2.80 | n-$C_5H_{11}$ | 3-Cl |
| 2.81 | n-$C_5H_{11}$ | 4-Cl |
| 2.82 | n-$C_5H_{11}$ | 3-CH$_3$ |
| 2.83 | n-$C_5H_{11}$ | 4-CH$_3$ |
| 2.84 | n-$C_5H_{11}$ | 4-CH(CH$_3$)$_2$ |
| 2.85 | n-$C_5H_{11}$ | 4-C(CH$_3$)$_3$ |
| 2.86 | n-$C_5H_{11}$ | 4-F |
| 2.87 | n-$C_6H_{13}$ | H |
| 2.88 | n-$C_6H_{13}$ | 3-Cl |
| 2.89 | n-$C_6H_{13}$ | 4-Cl |
| 2.90 | n-$C_6H_{13}$ | 3-CH$_3$ |
| 2.91 | n-$C_6H_{13}$ | 4-CH$_3$ |
| 2.92 | n-$C_6H_{13}$ | 4-CH(CH$_3$)$_2$ |
| 2.93 | n-$C_6H_{13}$ | 4-C(CH$_3$)$_3$ |
| 2.94 | n-$C_6H_{13}$ | 4-F |

The third group of the compounds (I) is represented by the formula IC:

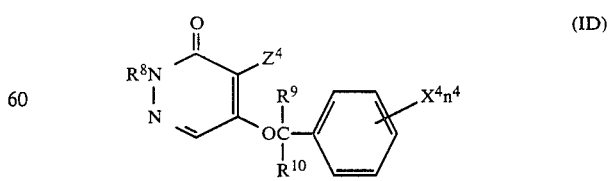

(IC)

wherein, $R^7$ denotes a straight or branched alkyl.

Among the compounds (IC), preferred are those wherein $R^7$ is a straight or branched alkyl having 1 to 6 carbon atoms such as methyl, ethyl, n-propyl, i-propyl, n-butyl, i-butyl, sec.-butyl, tert.-butyl, n-amyl, i-amyl, 1-ethyl-n-propyl, 2-methyl-n-butyl, 2-methyl-2-ethyl-ethyl or n-hexyl, particularly ethyl, n-propyl, i-propyl, n-butyl or tert.-butyl.

The cyclohexyl group is preferably located at 4-position.

The compounds (IC) are illustrated in Table 3.

TABLE 3

Compounds of the formula IC:

(IC)

| Compound No. | $R^7$ | Position of the cyclohexyl |
|---|---|---|
| 3.1 | methyl | 4-position |
| 3.2 | ethyl | " |
| 3.3 | n-propyl | " |
| 3.4 | i-propyl | " |
| 3.5 | n-butyl | " |
| 3.6 | i-butyl | " |
| 3.7 | s-butyl | " |
| 3.8 | t-butyl | " |
| 3.9 | n-amyl | " |
| 3.10 | i-amyl | " |
| 3.11 | 1-ethyl-n-propyl | " |
| 3.12 | 2-methyl-n-butyl | " |
| 3.13 | 2-methyl-2-ethyl-ethyl | " |
| 3.14 | n-hexyl | " |
| 3.15 | methyl | 3-position |
| 3.16 | ethyl | " |
| 3.17 | t-butyl | " |
| 3.18 | i-amyl | " |
| 3.19 | ethyl | 2-position |
| 3.20 | n-hexyl | " |

The fourth group of the compounds (I) is represented by the formula (ID):

(ID)

wherein, $R^8$ denotes an alkyl; $R^9$ and $R^{10}$ denote each independently hydrogen or a lower alkyl; $X^4$ denotes hydrogen, a lower alkyl, a halogen, cycloalkyl, trimethylsilyl,

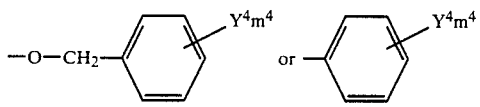

(wherein Y⁴ denotes hydrogen, a halogen, a lower alkyl, a lower alkoxy, a lower haloalkyl, a lower haloalkoxy or a cycloalkyl and $m^4$ is an integer of 1 to 5, said $Y^4$ being the same or different when $m^4$ is an integer of 2 to 5); $n^4$ is an integer of 1 to 3; and $Z^4$ is a halogen; said $X^4$ being the same or different when $n^4$ is 2 or 3 and the alkyls and the alkyl moieties contained in the groups being straight or branched.

Among the compounds (ID), preferred are those wherein $R^8$ is an alkyl of 1 to 6 carbon atoms, e.g. methyl, ethyl, n-propyl, i-propyl, n-butyl, sec.-butyl, tert.-butyl and n-hexyl, particularly ethyl, n-propyl, i-propyl or tert.-butyl; $R^9$ and $R^{10}$ are each independently hydrogen, an alkyl of 1 to 4 carbon atoms, e.g. methyl, ethyl, n-propyl, i-propyl and n-butyl, particularly hydrogen methyl or ethyl; $X^4$ is methyl, tert.-butyl, fluorine, chlorine, a cycloalkyl of 5 to 6 carbon atoms, trimethylsilyl,

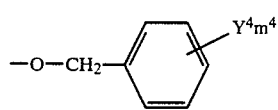

(wherein, $Y^4$ is hydrogen, fluorine, chlorine, methyl, ethyl, methoxy, trifluoromethyl, trifluoromethoxy, trifluoroethoxy (—OCH₂CF₃), or a cycloalkyl of 5 to 6 carbon atoms, and $m^4$ is 1 or 2), or

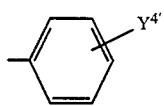

(wherein, $Y^{4'}$ is hydrogen, methyl, fluorine, chlorine or trifluoromethyl, trifluoromethoxy), $X^4$ is particularly methyl, tert.-butyl, fluorine, chlorine, trimethylsilyl, phenyl, benzyloxy unsubstituted or substituted by one chlorine atom, or cyclohexyl; n is 1 or 2; and $Z^4$ is chlorine or bromine, particularly chlorine.

The substituent $X^4$ is preferably located at 4-position. The compounds (ID) are illustrated in Table 4.

TABLE 4

Compounds of the formula ID:

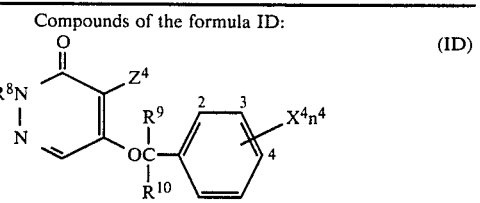

| Compound No. | $R^8$ | $R^9$ | $R^{10}$ | $X^4n^4$ | $Z^4$ |
|---|---|---|---|---|---|
| 4.1 | CH₃ | H | H | 3-Si(CH₃)₃ | Cl |
| 4.2 | CH₃ | CH₃ | H | 4-Si(CH₃)₃ | Cl |
| 4.3 | CH₃ | CH₃ | CH₃ | 4-Si(CH₃)₃ | Cl |
| 4.4 | CH₃ | H | H | 4-OCH₂C₆H₅ | Cl |
| 4.5 | CH₃ | H | H | 4-C₆H₅ | Cl |
| 4.6 | C₂H₅ | H | H | 4-Si(CH₃)₃ | Cl |
| 4.7 | C₂H₅ | CH₃ | H | 4-Si(CH₃)₃ | Cl |

TABLE 4-continued

Compounds of the formula ID:

| Compound No. | $R^8$ | $R^9$ | $R^{10}$ | $X^4n^4$ | $Z^4$ |
|---|---|---|---|---|---|
| 4.8 | C₂H₅ | C₂H₅ | H | 4-Si(CH₃)₃ | Cl |
| 4.9 | C₂H₅ | H | H | 4-OCH₂C₆H₅ | Cl |
| 4.10 | C₂H₅ | H | H | 4-OCH₂C₆H₄—m-Cl | Cl |
| 4.11 | C₂H₅ | H | H | 4-OCH₂C₆H₄—p-Cl | Cl |
| 4.12 | C₂H₅ | H | H | 2-OCH₂C₆H₄—o-CH₃ | Cl |
| 4.13 | C₂H₅ | H | H | 3-OCH₂C₆H₄—p-CH₃ | Cl |
| 4.14 | C₂H₅ | H | H | 4-C₆H₅ | Cl |
| 4.15 | C₂H₅ | H | H | 4-C₆H₄—p-CH₃ | Cl |
| 4.16 | C₂H₅ | CH₃ | H | 3-OCH₂C₆H₅ | Cl |
| 4.17 | C₂H₅ | C₂H₅ | CH₃ | 4-OCH₂C₆H₄—p-F | Cl |
| 4.18 | C₂H₅ | CH₃ | H | 4-C₆H₄—p-Cl | Cl |
| 4.19 | C₂H₅ | CH₃ | H | 4-OCH₂C₆H₄—p-OCF₃ | Cl |
| 4.20 | C₂H₅ | CH₃ | CH₃ | 3-C₆H₄—p-F | Cl |
| 4.21 | n-C₃H₇ | H | H | 2-Si(CH₃)₃ | Cl |
| 4.22 | n-C₃H₇ | H | H | 4-Si(CH₃)₃ | Cl |
| 4.23 | n-C₃H₇ | CH₃ | H | 4-Si(CH₃)₃ | Cl |
| 4.24 | n-C₃H₇ | C₂H₅ | CH₃ | 2-Si(CH₃)₃ | Cl |
| 4.25 | n-C₃H₇ | H | H | 3-OCH₂C₆H₅ | Cl |
| 4.26 | n-C₃H₇ | H | H | 4-OCH₂C₆H₅ | Cl |
| 4.27 | n-C₃H₇ | H | H | 4-OCH₂C₆H₄—p-OCH₃ | Cl |
| 4.28 | n-C₃H₇ | CH₃ | CH₃ | 4-OCH₂C₆H₄—p-OCH₂CF₃ | Cl |
| 4.29 | n-C₃H₇ | H | H | 4-C₆H₅ | Cl |
| 4.30 | n-C₃H₇ | C₂H₅ | H | 4-C₆H₄—p-CF₃ | Cl |
| 4.31 | i-C₃H₇ | H | H | 4-Si(CH₃)₃ | Cl |
| 4.32 | i-C₃H₇ | CH₃ | CH₃ | 4-Si(CH₃)₃ | Cl |
| 4.33 | i-C₃H₇ | H | H | 2-OCH₂C₆H₅ | Cl |
| 4.34 | i-C₃H₇ | H | H | 4-OCH₂C₆H₅ | Cl |
| 4.35 | i-C₃H₇ | H | H | 3-OCH₂C₆H₄—p-OCH₃ | Cl |
| 4.36 | i-C₃H₇ | C₂H₅ | H | 3-OCH₂C₆H₃—3,4-Cl₂ | Cl |
| 4.37 | i-C₃H₇ | n-C₄H₉ | CH₃ | 4-OCH₂C₆H₃—2,4-(CH₃)₂ | Cl |
| 4.38 | i-C₃H₇ | H | H | 4-C₆H₅ | Cl |
| 4.39 | i-C₃H₇ | i-C₃H₇ | H | 4-C₆H₅ | Cl |
| 4.40 | i-C₃H₇ | CH₃ | CH₃ | 4-C₆H₄—p-OCF₃ | Cl |
| 4.41 | n-C₄H₉ | H | H | 4-Si(CH₃)₃ | Cl |
| 4.42 | n-C₄H₉ | CH₃ | H | 4-Si(CH₃)₃ | Cl |
| 4.43 | n-C₄H₉ | n-C₄H₉ | CH₃ | 4-Si(CH₃)₃ | Cl |
| 4.44 | n-C₄H₉ | H | H | 4-OCH₂C₆H₅ | Cl |
| 4.45 | n-C₄H₉ | H | H | 2-OCH₂C₆H₄—o-OCH₃ | Cl |
| 4.46 | n-C₄H₉ | H | H | 2-OCH₂C₆H₄—p-C₂H₅ | Cl |
| 4.47 | n-C₄H₉ | CH₃ | H | 4-OCH₂C₆H₅ | Cl |
| 4.48 | n-C₄H₉ | C₂H₅ | H | 4-OCH₂C₆H₄—p-OCH₃ | Cl |
| 4.49 | n-C₄H₉ | H | H | 4-C₆H₅ | Cl |
| 4.50 | n-C₄H₉ | n-C₃H₇ | H | 4-C₆H₄—p-Cl | Cl |
| 4.51 | sec-C₄H₉ | H | H | 3-OCH₂C₆H₅ | Cl |
| 4.52 | sec-C₄H₉ | H | H | 3-OCH₂C₆H₄—p-cycloC₆H₁₁ | Cl |
| 4.53 | sec-C₄H₉ | H | H | 4-OCH₂C₆H₄—p-cycloC₅H₉ | Cl |
| 4.54 | sec-C₄H₉ | C₂H₅ | C₂H₅ | 4-C₆H₅ | Cl |
| 4.55 | t-C₄H₉ | H | H | 2-Si(CH₃)₃ | Cl |
| 4.56 | t-C₄H₉ | H | H | 4-Si(CH₃)₃ | Cl |
| 4.57 | t-C₄H₉ | CH₃ | H | 4-Si(CH₃)₃ | Cl |
| 4.58 | t-C₄H₉ | C₂H₅ | CH₃ | 4-Si(CH₃)₃ | Cl |
| 4.59 | t-C₄H₉ | H | H | 4-OCH₂C₆H₅ | Cl |
| 4.60 | t-C₄H₉ | H | H | 3-OCH₂C₆H₄—p-Cl | Cl |
| 4.61 | t-C₄H₉ | H | H | 4-OCH₂C₆H₄—p-cycloC₆H₁₁ | Cl |
| 4.62 | t-C₄H₉ | H | H | 4-OCH₂C₆H₄—o-CF₃ | Cl |
| 4.63 | t-C₄H₉ | H | H | 3-OCH₂C₆H₄—m-CH₃ | Cl |
| 4.64 | t-C₄H₉ | H | H | 4-OCH₂C₆H₄—p-OCH₃ | Cl |
| 4.65 | t-C₄H₉ | H | H | 2-OCH₂C₆H₃—2,4-Cl₂ | Cl |
| 4.66 | t-C₄H₉ | n-C₄H₉ | CH₃ | 4-OCH₂C₆H₅ | Cl |
| 4.67 | t-C₄H₉ | H | H | 4-C₆H₅ | Cl |
| 4.68 | t-C₄H₉ | H | H | 4-C₆H₄—p-F | Cl |
| 4.69 | t-C₄H₉ | H | H | 2-C₆H₄—o-CH₃ | Cl |
| 4.70 | t-C₄H₉ | CH₃ | H | 4-C₆H₅ | Cl |
| 4.71 | t-C₄H₉ | CH₃ | CH₃ | 4-C₆H₅ | Cl |
| 4.72 | n-C₆H₁₃ | H | H | 4-Si(CH₃)₃ | Cl |
| 4.73 | n-C₆H₁₃ | H | H | 4-Si(CH₃)₃ | Cl |
| 4.74 | n-C₆H₁₃ | H | H | 4-OCH₂C₆H₅ | Cl |
| 4.75 | n-C₆H₁₃ | CH₃ | H | 4-OCH₂C₆H₄—p-cycloC₆H₁₁ | Cl |
| 4.76 | n-C₆H₁₃ | H | H | 4-C₆H₅ | Cl |

TABLE 4-continued

Compounds of the formula ID:

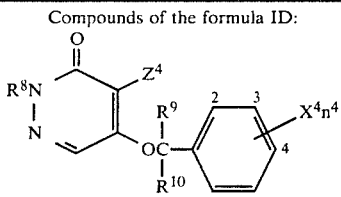

| Compound No. | R⁸ | R⁹ | R¹⁰ | X⁴n⁴ | Z⁴ |
|---|---|---|---|---|---|
| 4.77 | C₂H₅ | H | H | 4-F | Br |
| 4.78 | C₂H₅ | H | H | 4-Cl | Br |
| 4.79 | C₂H₅ | H | H | 4-CH₃ | Br |
| 4.80 | C₂H₅ | H | H | 4-t-C₄H₉ | Br |
| 4.81 | C₂H₅ | H | H | 3,4-Cl₂ | Br |
| 4.82 | i-C₃H₇ | H | H | 4-F | Br |
| 4.83 | i-C₃H₇ | H | H | 4-Cl | Br |
| 4.84 | i-C₃H₇ | H | H | 4-CH₃ | Br |
| 4.85 | i-C₃H₇ | H | H | 4-t-C₄H₉ | Br |
| 4.86 | i-C₃H₇ | H | H | 3,4-Cl₂ | Br |
| 4.87 | t-C₄H₉ | H | H | 4-F | Br |
| 4.88 | t-C₄H₉ | H | H | 4-t-C₄H₉ | Br |
| 4.89 | t-C₄H₉ | CH₃ | H | 4-cyclohexyl-H | Br |
| 4.90 | t-C₄H₉ | H | H | 4-OCH₂C₆H₄—p-Cl | Cl |
| 4.91 | t-C₄H₉ | H | H | 4-OCH₂C₆H₄—p-CH₃ | Cl |

The compounds listed in Tables 1 to 4 are given to illustrate the compounds of the present invention and not to restrict the invention. Compound numbers in these tables are also used in the description below.

The most important compounds of the invention are represented by the following formula:

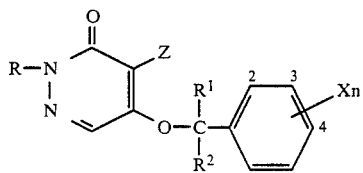

wherein R is t—C₄H₉, Z is Cl, R¹ is H, R² is H or CH₃, X is, at 4-position, CH₃, t—C₄H₉, F,

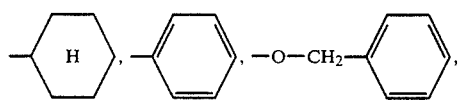

or —Si(CH₃)₃, and n is 1.

The compounds (I) may be prepared by reacting a 5-hydroxy-3(2H)-pyridazinone derivative of the formula II:

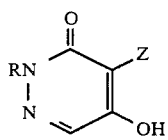

(wherein, R and Z are as defined in formula I) with a halide of the formula III:

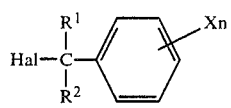

(wherein, Hal denotes a halogen, preferably chlorine bromine or iodine and more preferably chlorine or bromine, and R¹, R², X and n are as defined in formula I) according to the following reaction:

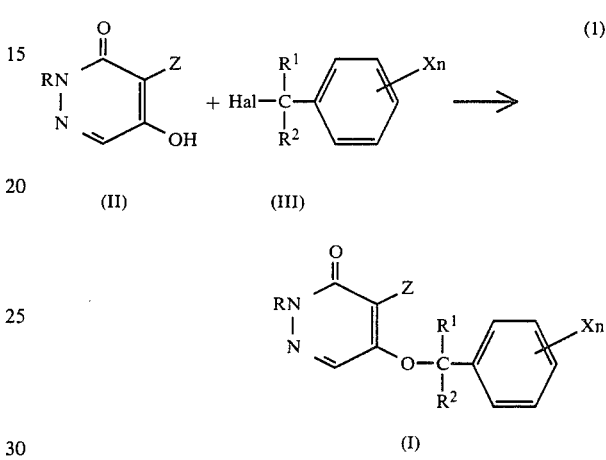

The reaction is preferably carried out in a solvent which does not take part in the reaction, i.e. an inert solvent, in the presence of a hydrogen halide-absorbing agent.

As the hydrogen halide-absorbing agent may be used inorganic bases such as sodium carbonate, potassium carbonate, metal hydroxides, e.g. sodium hydroxide, potassium hydroxide and calcium hydroxide, as well as organic bases such as triethylamine, pyridine and the like. Preferred hydrogen halide-absorbing agents are sodium carbonate, potassium carbonate and triethylamine. Such agent may be used usually in an amount of 0.5–5.0 moles per mole of the reactant of the formula II.

As the inert solvent may be used hydrocarbons such as benzene and toluene; lower alcohols such as methanol and ethanol; ketones such as acetone and methylethylketone; acetonitrile; dioxane; N,N-dimethylformamide and the like. Preferred solvents are acetone, acetonitrile and N,N-dimethylformamide.

A 2-alkyl-4-halo-5-hydroxy-3(2H)-pyridazinone (II) and a halide (III) may be reacted usually in a molar ratio of 1:0.5 to 1:2, preferably 1:1 to 1:1.5.

The reaction temperature may range from room temperature to the boiling point of the solvent employed in the reaction, preferably from 80° C. to 140° C.

The 5-hydroxy-3(2H)-pyridazinone derivative used in reaction (1) may be obtained by first preparing a 4,5-dihalogeno-3(2H)-pyridazinone derivative of the formula VI according to a conventional synthesis indicated below as reaction (2) (a) or (2) (b), and then converting the chlorine atom at 5-position to hydroxy group according to reaction (3) shown below:

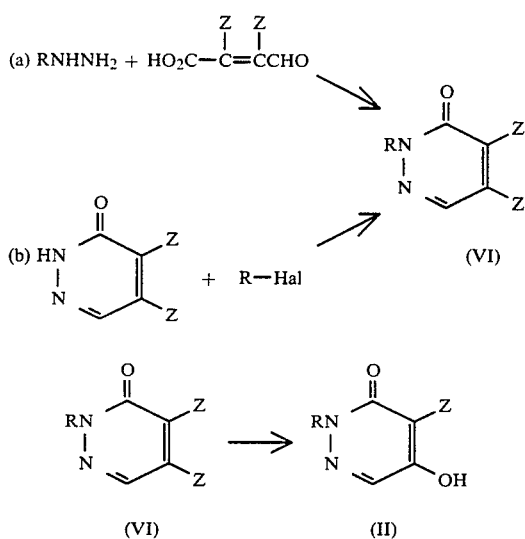

(a) $RNHNH_2 + HO_2C-\underset{Z}{C}=\underset{Z}{C}CHO$  (2)

(b) (VI) + R—Hal (VI) → (II)  (3)

wherein, R and Z are as defined in formula I, and Hal. denotes a halogen, preferably chlorine or bromine.

The reaction (2) (a) above is a cyclization reaction of a substituted hydrazine (which may be a salt with a suitable acid) with an acid

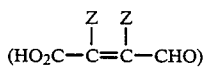
$(HO_2C-\underset{Z}{C}=\underset{Z}{C}-CHO)$ to synthesize a compound (VI). On the other hand, the reaction (2) (b) is an alkylation of a 4,5-dihalogeno-3(2H)-pyridazinone with an alkyl halide (R-Hal).

Alternatively, in some cases the compounds (I) may be synthesized, according to the following reaction (4), by reacting a 2-alkyl-4,5-dihalogeno-3(2H)-pyridazinone derivative (VI) with an alcoholate of the formula (VII):

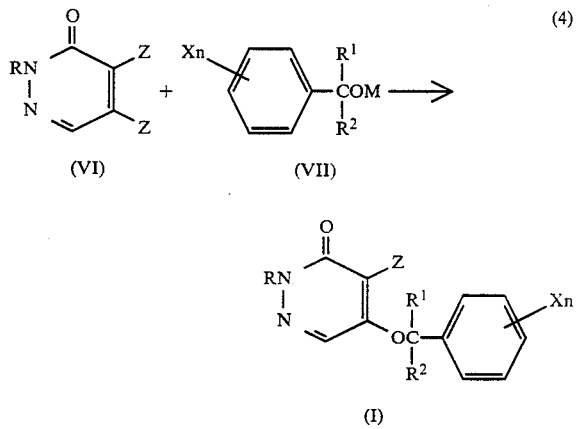

wherein, R, $R^1$, $R^2$, Z, X and n are as previously defined in formula I and M is an alkali metal, preferably sodium or potassium.

It is preferred from the viewpoint of yield to synthesize the compounds (I) according to reaction (1) rather than reaction (4).

Preferred reactants (II) and (III) used in reaction (1) are those which yield preferred compounds of the formula I or any of formula IA-ID.

The compounds (IA), (IB), (IC) or (ID) may be obtained in a way similar to the above by using the corresponding reactants of the formulae (II) and (III).

Preparation of the compounds (I) of the invention is described more in detail by way of the following examples which are not to restrict the invention.

SYNTHESIS EXAMPLE 1

Synthesis of 2-tert.-butyl-4-chloro-5-(4,α-dimethylbenzyloxy)-3-(2H)-pyridazinone (Compound No. 1.78)

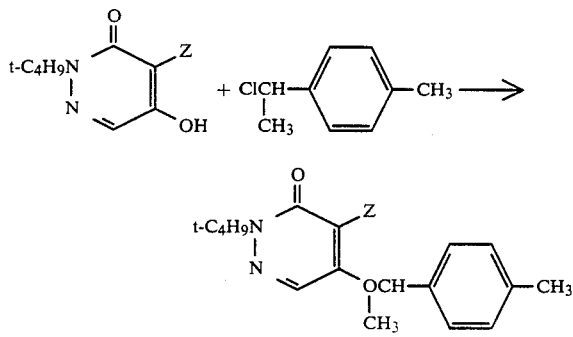

1.5 g of anhydrous potassium carbonate and 1.3 g of 4-(α-chloroethyl)toluene were added to 1.5 g of 2-tert.-butyl-4-chloro-5-hydroxy-3(2H)-pyridazinone dissolved into 10 ml of N,N-dimethylformamide, and the resulting mixture was heated under stirring in an oil bath of 80° to 110° C. for 4 hours. After being allowed to cool to room temperature, 100 ml of water was added to the reaction mixture, followed by stirring. Oily matter separated from the reaction mixture was extracted with 50 ml of chloroform. The aqueous layer was extracted with 30 ml of chloroform again, the chloroform layers were combined, washed with water, and dried over anhydrous sodium sulfate. Chloroform was distilled off under reduced pressure, and the residue was recrystallized from isopropyl ether-petroleum ether mixer to obtain 1.1 g of the intended compound (Compound No. 1.78) having m.p. 104°-105.5° C. (yield: 48.1%)

When measured in deutro chloroform, $^1$H-NMR spectrum of the compound thus obtained is as follows:

| δ (ppm) | Attribution |
|---|---|
| 5.46 (q, 1H) | —OC$\underline{H}$(CH$_3$)— |
| 7.53 (s, 1H) | $\underline{H}$ at 6-position of 3(2H)—pyridazinone ring |

From the above data, the compound in this example was identified as the captioned one.

Similarly to the process in Synthesis Example 1, the compounds shown in Table I were synthesized. The identification of the compounds was made similarly to Synthesis Example 1.

TABLE I

Compounds of the formula:

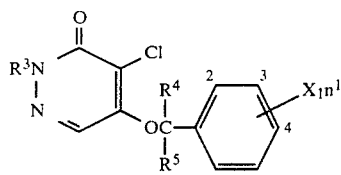

| Compound No. | $R^3$ | $R^4$ | $R^5$ | $X_1n^1$ | m.p. (°C.) | $OC\underline{H}-$ (δ ppm) | $\underline{H}$ (δ ppm) |
|---|---|---|---|---|---|---|---|
| 1.9  | $C_2H_5$   | $CH_3$   | H | 3-Cl            | —           | 5.52 (q) | 7.61 (s) |
| 1.10 | $C_2H_5$   | $CH_3$   | H | 4-F             | 95–96.5     | 5.54 (q) | 7.59 (s) |
| 1.11 | $C_2H_5$   | $CH_3$   | H | 4-Cl            | —           | 5.51 (q) | 7.56 (s) |
| 1.12 | $C_2H_5$   | $CH_3$   | H | 4-Br            | 94–95       | 5.49 (q) | 7.55 (s) |
| 1.13 | $C_2H_5$   | $Ch_3$   | H | 3-$CH_3$        | —           | 5.45 (q) | 7.58 (s) |
| 1.15 | $C_2H_5$   | $CH_3$   | H | 4-$CH_3$        | —           | 5.48 (q) | 7.60 (s) |
| 1.16 | $C_2H_5$   | $CH_3$   | H | 4-i-$C_3H_7$    | 85–86       | 5.50 (q) | 7.60 (s) |
| 1.17 | $C_2H_5$   | $CH_3$   | H | 4-t-$C_4H_9$    | —           | 5.56 (q) | 7.67 (s) |
| 1.19 | $C_2H_5$   | $CH_3$   | H | 4-cyclo-$C_6H_{11}$ | —       | 5.53 (q) | 7.66 (s) |
| 1.20 | $C_2H_5$   | $C_2H_5$ | H | H               | —           | 5.28 (t) | 7.58 (s) |
| 1.21 | $C_2H_5$   | $C_2H_5$ | H | 4-Cl            | —           | 5.27 (t) | 7.55 (s) |
| 1.22 | $C_2H_5$   | $C_2H_5$ | H | 4-$CH_3$        | —           | 5.21 (t) | 7.58 (s) |
| 1.23 | $C_2H_5$   | $C_2H_5$ | H | 4-t-$C_4H_9$    | —           | 5.23 (t) | 7.60 (s) |
| 1.24 | $C_2H_5$   | $C_2H_5$ | H | 4-cyclo-$C_6H_{11}$ | —       | 5.21 (t) | 7.58 (s) |
| 1.29 | n-$C_3H_7$ | $CH_3$   | H | 4-t-$C_4H_9$    | —           | 5.50 (q) | 7.60 (s) |
| 1.37 | i-$C_3H_7$ | $CH_3$   | H | H               | —           | 5.47 (m) | 7.58 (s) |
| 1.38 | i-$C_3H_7$ | $CH_3$   | H | 4-t-$C_4H_9$    | —           | 5.49 (m) | 7.66 (s) |
| 1.39 | i-$C_3H_7$ | $CH_3$   | H | 4-cyclo-$C_6H_{11}$ | —       | 5.48 (m) | 7.54 (s) |
| 1.46 | n-$C_4H_9$ | $CH_3$   | H | 4-t-$C_4H_9$    | —           | 5.48 (q) | 7.59 (s) |
| 1.47 | n-$C_4H_9$ | $CH_3$   | H | 4-cyclo-$C_6H_{11}$ | —       | 5.47 (q) | 7.57 (s) |
| 1.72 | t-$C_4H_9$ | $CH_3$   | H | H               | 103–104     | 5.48 (q) | 7.50 (s) |
| 1.73 | t-$C_4H_9$ | $CH_3$   | H | 4-F             | —           | 5.52 (q) | 7.55 (s) |
| 1.75 | t-$C_4H_9$ | $CH_3$   | H | 4-Cl            | 105.5–106.5 | 5.47 (q) | 7.50 (s) |
| 1.76 | t-$C_4H_9$ | $CH_3$   | H | 4-Br            | 147–149     | 5.47 (q) | 7.51 (s) |
| 1.77 | t-$C_4H_9$ | $CH_3$   | H | 3-$CH_3$        | 117.5–118.5 | 5.42 (q) | 7.51 (s) |
| 1.79 | t-$C_4H_9$ | $CH_3$   | H | 4-i-$C_3H_7$    | —           | 5.50 (q) | 7.58 (s) |
| 1.80 | t-$C_4H_9$ | $CH_3$   | H | 4-t-$C_4H_9$    | —           | 5.47 (q) | 7.56 (s) |
| 1.81 | t-$C_4H_9$ | $CH_3$   | H | 4-cyclo-$C_6H_{11}$ | 101–104 | 5.45 (q) | 7.51 (s) |
| 1.84 | t-$C_4H_9$ | $C_2H_5$ | H | H               | 95–96       | 5.30 (t) | 7.49 (s) |
| 1.85 | t-$C_4H_9$ | $C_2H_5$ | H | 4-Cl            | —           | 5.25 (t) | 7.50 (s) |
| 1.86 | t-$C_4H_9$ | $C_2H_5$ | H | 4-$CH_3$        | 96–97       | 5.14 (t) | 7.48 (s) |
| 1.87 | t-$C_4H_9$ | $C_2H_5$ | H | 4-t-$C_4H_9$    | —           | 5.18 (t) | 7.52 (s) |
| 1.88 | t-$C_4H_9$ | $C_2H_5$ | H | 4-cyclo-$C_6H_{11}$ | 122–123 | 5.04 (t) | 7.40 (s) |

SYNTHESIS EXAMPLE 2

Synthesis of 4-chloro-5-(4-methylbenzyloxy)-2-iso-propyl-3-(2H)-pyridazinone (Compound No. 2.44)

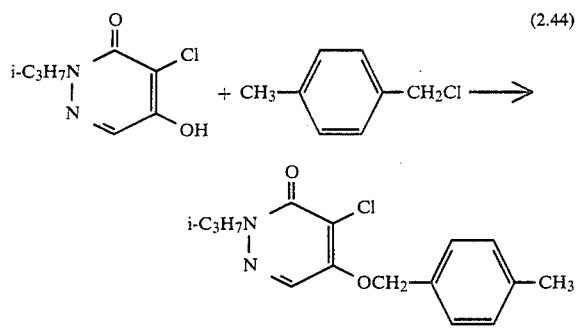

1.89 g (10 m mole) of 4-chloro-5-hydroxy-2-i-propyl-3(2H)-pyridazinone, 2.8 g (about 20 m mole) of anhydrous potassium carbonate and 20 ml of N,N-dimethylformamide were mixed together at room temperature. 1.70 g (12 m mole) of 4-methylbenzylchloride was added to the mixture and heated at 120°–130° C. for 2 hours under stirring.

After the reaction mixture was allowed to cool, 100 ml of water was added thereto and the mixture was vigorously stirred at room temperature for 30 minutes. Precipitated crude product were filtered, washed with water and dried. The crude product was recrystallized from 90% methanol to obtain 2.22 g of colorless needle-like compound (Compound No. 2.44) (yield: 76%).

The identification of this compound was made by $^1$H-NMR spectrum. The spectrum of the product in $CDCl_3$ solution (δppm) and their attribution are as follows:

1.33 (d,6H, ($C\underline{H}_3$)$_2$)

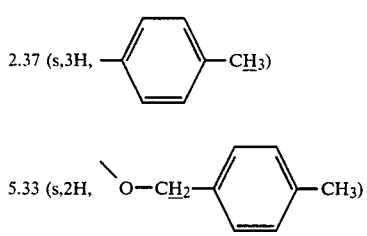

2.37 (s,3H, —⟨C₆H₄⟩—CH₃)

5.33 (s,2H, \O—CH₂—⟨C₆H₄⟩—CH₃)

Similarly to the process in Synthesis Example 2, the compounds shown in Table II were synthesized. The identification in chemical structure of these compounds was made similarly to Synthesis Example 2.

TABLE II

Compounds of the formula (IB)

$$\text{(IB)}$$

| Compound No | $R^6$ | $X^2n^2$ | m.p. (°C.) |
|---|---|---|---|
| 2.1 | $CH_3$ | H | 134–135 |
| 2.2 | $CH_3$ | 3-Cl | 144–145 |
| 2.3 | $CH_3$ | 4-Cl | 153–155 |
| 2.5 | $CH_3$ | 4-$CH_3$ | 145–146 |
| 2.8 | $CH_3$ | 4-F | 123–124 |
| 2.10 | $CH_3$ | 4-$OCH_3$ | 147–148 |
| 2.11 | $CH_3$ | 2,4-$Cl_2$ | 162–163 |
| 2.12 | $CH_3$ | 3,4-$Cl_2$ | 195–196 |
| 2.14 | $C_2H_5$ | H | 112–114 |
| 2.15 | $C_2H_5$ | 3-Cl | 132–134 |
| 2.16 | $C_2H_5$ | 4-Cl | 129–130 |
| 2.17 | $C_2H_5$ | 3-$CH_3$ | 97–98 |
| 2.18 | $C_2H_5$ | 4-$CH_3$ | 137–138 |
| 2.19 | $C_2H_5$ | 4-$CH(CH_3)_2$ | 79–81 |
| 2.20 | $C_2H_5$ | 4-$C(CH_3)_3$ | 102–104 |
| 2.21 | $C_2H_5$ | 4-F | 120–121 |
| 2.22 | $C_2H_5$ | 4-Br | 125–127 |
| 2.23 | $C_2H_5$ | 4-$OCH_3$ | 136–138 |
| 2.24 | $C_2H_5$ | 2,4-$Cl_2$ | 131–132 |
| 2.25 | $C_2H_5$ | 3,4-$Cl_2$ | 181–183 |
| 2.27 | n-$C_3H_7$ | H | 93–95 |
| 2.28 | n-$C_3H_7$ | 3-Cl | 125–126 |
| 2.29 | n-$C_3H_7$ | 4-Cl | 103–104 |
| 2.30 | n-$C_3H_7$ | 3-$CH_3$ | 99–100 |
| 2.31 | n-$C_3H_7$ | 4-$CH_3$ | 106–107 |
| 2.34 | n-$C_3H_7$ | 4-F | 132–133 |
| 2.35 | n-$C_3H_7$ | 4-Br | 105–106 |
| 2.36 | n-$C_3H_7$ | 4-$OCH_3$ | 113–114 |
| 2.40 | i-$C_3H_7$ | H | 166–168 |
| 2.41 | i-$C_3H_7$ | 3-Cl | 182–184 |
| 2.42 | i-$C_3H_7$ | 4-Cl | 159–162 |
| 2.43 | i-$C_3H_7$ | 3-$CH_3$ | 136–137 |
| 2.44 | i-$C_3H_7$ | 4-$CH_3$ | 139–141 |
| 2.45 | i-$C_3H_7$ | 4-$CH(CH_3)_2$ | 171–172 |
| 2.46 | i-$C_3H_7$ | 4-$C(CH_3)_3$ | 192–194 |
| 2.47 | i-$C_3H_7$ | 4-F | 185–187 |
| 2.48 | i-$C_3H_7$ | 4-Br | 152–153 |
| 2.49 | i-$C_3H_7$ | 4-$OCH_3$ | 134–136 |
| 2.50 | i-$C_3H_7$ | 2,4-$Cl_2$ | 137–138 |
| 2.51 | i-$C_3H_7$ | 3,4-$Cl_2$ | 195–197 |
| 2.53 | n-$C_4H_9$ | H | 100–101 |
| 2.55 | n-$C_4H_9$ | 4-Cl | 112–113 |
| 2.56 | n-$C_4H_9$ | 3-$CH_3$ | 76–77 |
| 2.57 | n-$C_4H_9$ | 4-$CH_3$ | 97–98 |
| 2.60 | n-$C_4H_9$ | 4-F | 144–145 |
| 2.61 | n-$C_4H_9$ | 4-Br | 100–102 |
| 2.62 | n-$C_4H_9$ | 4-$OCH_3$ | 92–93 |
| 2.63 | n-$C_4H_9$ | 2,4-$Cl_2$ | 112–113 |
| 2.66 | t-$C_4H_9$ | H | 78–79 |
| 2.68 | t-$C_4H_9$ | 4-Cl | 126–127 |
| 2.69 | t-$C_4H_9$ | 3-$CH_3$ | 116–117 |

TABLE II-continued

Compounds of the formula (IB)

$$\text{(IB)}$$

| Compound No | $R^6$ | $X^2n^2$ | m.p. (°C.) |
|---|---|---|---|
| 2.70 | t-$C_4H_9$ | 4-$CH_3$ | 129–130 |
| 2.71 | t-$C_4H_9$ | 4-$CH(CH_3)_2$ | 122–123 |
| 2.72 | t-$C_4H_9$ | 4-$C(CH_3)_3$ | 125–126 |
| 2.73 | t-$C_4H_9$ | 4-F | 82–83 |
| 2.74 | t-$C_4H_9$ | 4-Br | 140–141 |
| 2.75 | t-$C_4H_9$ | 4-$OCH_3$ | 127–128 |
| 2.76 | t-$C_4H_9$ | 2,4-$Cl_2$ | 121–123 |
| 2.77 | t-$C_4H_9$ | 3,4-$Cl_2$ | 164–166 |
| 2.78 | t-$C_4H_9$ | 3,4-$(CH_3)_2$ | 183–185 |
| 2.89 | n-$C_6H_{13}$ | 4-Cl | 102–103 |
| 2.91 | n-$C_6H_{13}$ | 4-$CH_3$ | 102–103 |
| 2.92 | n-$C_6H_{13}$ | 4-$CH(CH_3)_2$ | 97–98 |
| 2.94 | n-$C_6H_{13}$ | 4-F | 105–107 |

SYNTHESIS EXAMPLE 3

Synthesis of 4-chloro-5-(p-cyclohexylbenzyloxy)-2-ethyl-3-(2H)-pyridazinone (Compound No. 3.2)

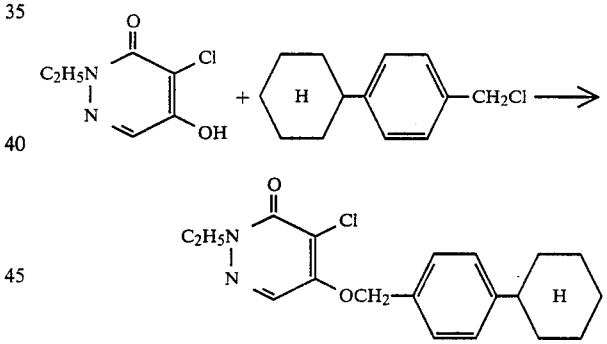

2.32 g (11 m mole) of p-cyclohexylbenzylchloride was added to a mixture of 1.75 g (10 m mole) of 4-chloro-2-ethyl-5-hydroxy-3(2H)pyridazinone, 2.8 g (about 20 m mole) of anhydrous potassium carbonate and 20 ml of N,N-dimethylformamide, and the resulting mixture was heated at 120°–130° C. for 2 hours under stirring.

After the reaction mixture was allowed to cool, 100 ml of water was added to it, and the precipitated solid was filtered and washed with water. The product was recrystallized from a mixed solvent of n-hexane and ethyl acetate to obtain 2.50 g of the intended product of the invention, melting point: 168°–170° C., yield: 72%.

The product thus obtained was identified as captioned one as follows:

¹H-NMR spectrum (in CDCl₃ solution): δ(ppm) 7.78 (H at 6-position of pyridazone ring)

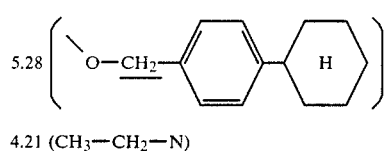

4.21 (CH$_3$—CH$_2$—N)

IR SPECTRUM: 1620 cm$^{-1}$ ($\nu_{c=o}$)

Similarly to the Synthesis Example 3, the compounds shown in Table III were synthesized.

The chemical structures of the compounds were similarly identified as in Synthesis Example 3.

TABLE III

The compounds of the formula (IC):

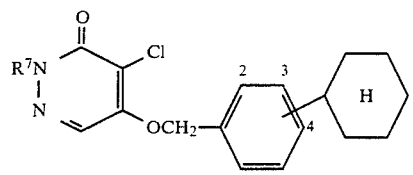

(IC)

| Compound No. | R$^7$ | Position of the cyclohexyl | m.p. (°C.) | Yield (%) |
|---|---|---|---|---|
| 3.3 | n-propyl | 4-position | 120–121.5 | 80.0 |
| 3.4 | i-propyl | " | 185–187 | 88.4 |
| 3.5 | n-butyl | " | 107–108 | 81.1 |
| 3.8 | t-butyl | " | 161–163 | 90.3 |

SYNTHESIS EXAMPLE 4

Synthesis of 4-chloro-2-ethyl-5-(p-trimethylsilylbenzyloxy)-3-(2H)-pyridazinone (Compound 4.6)

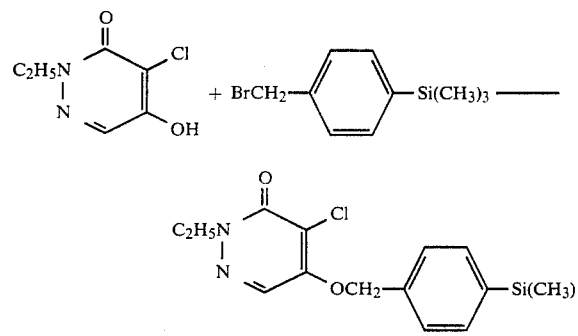

1.8 g of anhydrous potassium carbonate and 2.1 g of p-trimethylsilylbenzylbromide were added to 1.5 g of 4-chloro-2-ethyl-5-hydroxy-3(2H)-pyridazinone dissolved in 10 ml of N,N-dimethylformamide, and the resulting mixture was heated in an oil bath of 120°–130° C. for 2 hours. After the reaction mixture was allowed to cool to room temperature, 100 ml of water was added thereto and the mixture was stirred vigorously. Precipitate was filtered, washed with water and dried to obtain 1.7 g of a crude product. The product was recrystallized from a mixed solvent of isopropyl ether and ethyl acetate to obtain the intended compound (Compound No. 4.6) having m.p. 122°–125° C. (yield: 44.8%).

SYNTHESIS EXAMPLE 5

Synthesis of 2-tert.-butyl-4-chloro-5-(p-phenyl)-benzyloxy-3(2H)-pyridazinone (Compound No. 4.67)

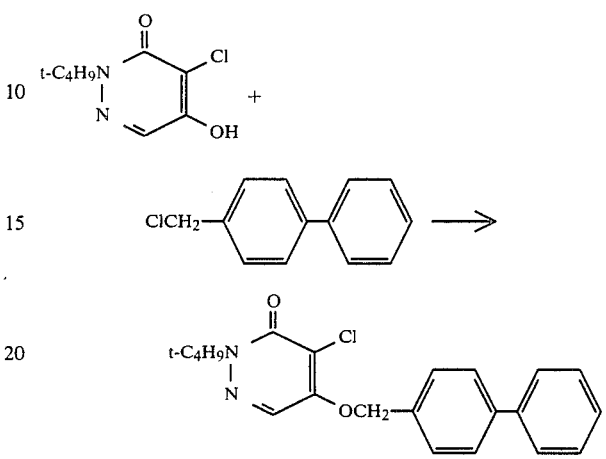

2.03 g (10 m mole) of p-chloromethylbiphenyl was added to a mixture of 2.03 g (10 m mole) of 2-tert.-butyl-4-chloro-5-hydroxy-3(2H)-pyridazinone, 2.1 g (about 15 m mole) of anhydrous potassium carbonate and 20 ml of N,N-dimethylformamide, and the resulting mixture was heated in an oil bath of 100° C. for 1.5 hours under stirring. After the reaction mixture was allowed to cool, 100 ml of water was added to it and the mixture was stirred vigorously. Precipitate was filtered and washed with water. Then, it was recrystallized from ethanol to obtain 2.32 g of white crystal of m.p. 197°–200° C. (yield: 63%).

Similarly to Synthesis Examples 4 and 5, the compounds shown in Table IV were synthesized.

TABLE IV

Compounds of the formula: (ID)

| Compound No. | m.p. (°C.) |
|---|---|
| 4.9 | 120–122 |
| 4.14 | 150–154 |
| 4.26 | 99–100 |
| 4.56 | 116–118 |
| 4.57 | (glassy matter) |
| 4.59 | 123–125 |
| 4.77 | 118.5–119.5 |
| 4.78 | 124.5–126 |
| 4.79 | 117–118 |
| 4.80 | 130–132 |
| 4.81 | 155–156 |
| 4.82 | 172–173 |
| 4.83 | 162–164 |
| 4.84 | 106–107 |
| 4.85 | 170–172 |
| 4.86 | 178–179 |
| 4.87 | 76–77 |
| 4.88 | 124–125 |
| 4.89 | (glassy matter) |
| 4.90 | 155–162 |
| 4.91 | 86–89 |

The compounds according to the present invention exhibit pesticidal activities such as fungicidal, insecticidal, acaricidal and/or nematicidal activities, and, therefore, are employable as agricultural and horticultural fungicidal, insecticidal, acaricidal, and/or nematicidal agent and the like.

When used as agricultural and horticultural fungicidal, insecticidal, acaricidal, nematicidal agents, the compounds according to the present invention may be generally mixed with an appropriate carrier, for instance, a solid carrier such as clay, talc, bentonite or diatomaceous earth, or a liquid carrier such as water, alcohols (e.g. methanol and ethanol), ketones (e.g. acetone), ethers, aliphatic hydrocarbons, aromatic hydrocarbons (e.g. benzene, toluene and xylene), acid amides (e.g. dimethylformamide), esters or nitriles. If desired, to this mixture may be added emulsifier, dispersing agent, suspension agent, penetrating agent, spreader, stabilizer and the like to put it into practical use in a form of liquid preparation, emulsifiable concentrate, wettable powder, dust or the like.

The effective amount of each of the compounds according to the present invention for agricultural or horticultural fungicidal, insecticidal, acaricidal and/or nematicidal agent is from 0.05 to 90 wt %, preferably, from 0.1 to 75 wt % as a concentrated composition with respect to the total amount thereof. When in use, it is diluted with water, alcohol or the like up to a desired concentration.

The compounds which are preferable as an active ingredient of the pesticidal composition are the same as mentioned above in connection with the preferred embodiments of the compounds per se of the present invention.

Next, some formulation examples of the compounds according to the present invention are specifically recited below, but the present invention is not restricted to them. In the following, "part" in the formulations means "part by weight".

FORMULATION EXAMPLE 1

Emulsifiable Concentrates

| | |
|---|---|
| Active ingredient | 50 parts |
| Xylene | 25 parts |
| N,N—dimethylformamide | 20 parts |
| Solpol 2680* (trade name, active surface agent manufactured by Toho Chemicals, Co., Ltd.) | 5 parts |

*Solpol 2680 is a mixture of a non-ionic active surface agent and an anionic active surface agent The above components are mixed intimately together to form an emulsifiable concentrate. When in use, the emulsifiable concentrate is diluted with water up to one five hundredth to one twenty thousandth in concentration for spraying.

FORMULATION EXAMPLE 2

Wettable Powders

| | |
|---|---|
| Active ingredient | 25 parts |
| Siegreit A (trade name, caoline base clay manufactured by Siegreit Mining Industries Co., Ltd.) | 69 parts |
| Solpol 5039* (trade name, active surface agent manufactured by Toho Chemical Co., Ltd.) | 3 parts |
| Carplex (trade name, coagulation inhibition agent white carbon manufactured by Shionogi Seiyaku K.K.) | 3 parts |

*Solpol 5039 is a mixture of a non-ionic active surface agent and an anionic active surface agent.

The above components are homogeneously mixed together to form a wettable powder. When in use, the wettable powder is diluted with water up to one five hundredth to one twenty thousandth for spraying.

FORMULATION EXAMPLE 3

Oil Solutions

| | |
|---|---|
| Active ingredient | 50 parts |
| methylcellosolve | 50 parts |

The above components are homogeneously mixed together to form an oil solution. The above oil solution is applied to channels or water pools at a rate of 0.1 to 50 ml per 1 $m^2$ or sprayed from airplane at a rate of 10–1000 ml per 10 acres.

FORMULATION EXAMPLE 4

Dusts

| | |
|---|---|
| Active ingredient | 3.0 parts |
| Carplex (coagulation inhibition agent) | 0.5 parts |
| Clay | 95 parts |
| di-isopropyl phosphate | 1.5 parts |

The above components are homogeneously mixed together to form a dust. When in use, the dust is sprayed at a rate of 0.03 to 15 kg per 10 acres.

Next, the effects of the compounds according to the present invention will be discussed with reference to the following biological tests.

TEST EXAMPLE 1

Test for Controlling Downy Mildew of Cucumber

Employing cucumbers (*Cucumis sativus* L.: variety Sagamihanjiro) which had been grown for about 2 weeks, a solution of a predetermined concentration of each compound according to the present invention was sprayed at the rate of 20 ml per pot. After each pot was placed overnight in a greenhouse, a suspension of spores of *Pseudoperonospora cubensis* (the concentration of the spores being such that when observed by a 150 magnification microscope, 15 pieces of the spore may be present) was sprayed to the cucumbers for inoculation. The cucumbers to which the spores of *Pseudoperonospora cubensis* had been inoculated were left for 24 hours in a room kept at 25° C. with a relative humidity of 100% and then transported to a greenhouse for observation of disease appearance. Seven days after the inoculation, the percentages of the disease appearance were measured. The results are shown in Table 5. The figures in Table 5 showing the degree of the disease appearance mean the following:

0 no disease appearance
1 disease appearance being less than 5% of the inoculated leaves
2 disease appearance being 6–20% of the inoculated leaves
3 disease appearance being 21–50% of the inoculated leaves -continued 4 disease appearance being 51-90% of the inoculated leaves
5 disease appearance being more than 90% of the inoculated leaves

TABLE 5

| Compound No. | Spray concentration (ppm) | Degree of disease appearance |
|---|---|---|
| 1.9 | 500 | 3 |
| 1.10 | " | 2 |
| 1.11 | " | 0 |
| 1.12 | " | 2 |
| 1.15 | " | 2 |
| 1.16 | " | 3 |
| 1.19 | " | 1 |
| 1.20 | " | 3 |
| 1.22 | " | 2 |
| 1.23 | " | 1 |
| 1.24 | " | 1 |
| 1.29 | " | 1 |
| 1.38 | " | 0 |
| 1.39 | " | 3 |
| 1.46 | " | 3 |
| 1.47 | " | 3 |
| 1.73 | " | 0 |
| 1.75 | " | 1 |
| 1.76 | " | 1 |
| 1.78 | " | 0 |
| 1.79 | " | 3 |
| 1.80 | " | 0 |
| 1.81 | " | 0 |
| 1.84 | " | 0 |
| 1.86 | " | 2 |
| 1.87 | " | 1 |
| 2.29 | " | 1 |
| 2.55 | " | 1 |
| 2.60 | " | 1 |
| 2.68 | " | 0 |
| 2.69 | " | 0 |
| 2.73 | " | 0 |
| 2.74 | " | 0 |
| 2.76 | " | 1 |
| 3.2 | " | 3 |
| 3.3 | " | 0 |
| 3.4 | " | 3 |
| 3.5 | " | 2 |
| 4.6 | " | 1 |
| 4.14 | " | 1 |
| 4.57 | " | 0 |
| 4.59 | " | 1 |
| 4.67 | " | 2 |
| 4.78 | " | 0 |
| 4.79 | " | 0 |
| 4.80 | " | 0 |
| 4.81 | " | 2 |
| Non-treated | — | 5 |

TEST EXAMPLE 2

Test for Controlling Powdery Mildew of Cucumber

Employing cucumbers (*Cucumis sativus* L.: variety Sagamihanjiro) which had been grown in pots for about 2 weeks, a solution of a predetermined concentration of each compound according to the present invention was sprayed at the rate of 20 ml per pot. After each pot was placed overnight in a greenhouse, a suspension of spores of *Sphaerotheca fuliginea* (the concentration of the spores being such that when observed by a 150 magnification microscope, 25 pieces of the spores may be present) was sprayed to the cucumbers for inoculation. The cucumbers were placed in a greenhouse of 25°–30° C. for observation of disease appearance. Ten days after the inoculation, the percentages of the disease appearance were measured. The results are shown in Table 6.

The figures in Table 6 showing the degree of the disease appearance are the same as in Test Example 1.

TABLE 6

| Compound No. | Concentration (ppm) | Degree of disease appearance |
|---|---|---|
| 1.9 | 500 | 2 |
| 1.10 | " | 1 |
| 1.11 | " | 0 |
| 1.12 | " | 2 |
| 1.13 | " | 3 |
| 1.15 | " | 2 |
| 1.16 | " | 3 |
| 1.17 | " | 2 |
| 1.19 | " | 0 |
| 1.20 | " | 2 |
| 1.22 | " | 0 |
| 1.23 | " | 3 |
| 1.24 | " | 2 |
| 1.29 | " | 1 |
| 1.38 | " | 3 |
| 1.39 | " | 3 |
| 1.46 | " | 2 |
| 1.47 | " | 3 |
| 1.72 | " | 0 |
| 1.73 | " | 0 |
| 1.77 | " | 0 |
| 1.76 | " | 3 |
| 1.79 | " | 0 |
| 1.80 | " | 0 |
| 1.81 | " | 0 |
| 1.84 | " | 0 |
| 1.86 | " | 0 |
| 1.87 | " | 3 |
| 2.29 | " | 2 |
| 2.30 | " | 2 |
| 2.31 | " | 2 |
| 2.34 | " | 1 |
| 2.35 | " | 2 |
| 2.53 | " | 3 |
| 2.62 | " | 3 |
| 2.68 | " | 0 |
| 2.69 | " | 0 |
| 2.70 | " | 0 |
| 2.71 | " | 0 |
| 2.73 | " | 0 |
| 2.74 | " | 0 |
| 2.78 | " | 0 |
| 3.2 | " | 2 |
| 3.3 | " | 0 |
| 3.4 | " | 3 |
| 3.5 | " | 0 |
| 3.8 | " | 0 |
| 4.6 | " | 0 |
| 4.14 | " | 0 |
| 4.56 | " | 0 |
| 4.57 | " | 0 |
| 4.67 | " | 0 |
| 4.77 | " | 2 |
| 4.78 | " | 2 |
| 4.79 | " | 0 |
| 4.80 | " | 1 |
| 4.81 | " | 2 |
| Non-treated | — | 5 |

TEST EXAMPLE 3

Insecticidal Test on House Fly (*Musca domestica*) Adult

One ml of acetone solution containing 1000 ppm of the compound to be tested was added dropwise to a laboratory dish of 9 cm in diameter so that the solution may be evenly spread over the dish. After completely evaporating the acetone at room temperature, ten house fly adults were placed in the dish and then the dish was covered with a plastic cap provided with some pores. The dish containing the adults was placed in a thermostatic chamber kept at 25° C. An evaluation was made after 48 hours by counting the adults killed and calculating the mortality of adults in accordance with the following equation:

$$\text{Mortality} = \frac{\text{number of adult killed}}{\text{number of adult placed}} \times 100$$

The results thereof are listed in Table 7.
Incidentally, each test was repeated twice.

TEST EXAMPLE 4

Insecticidal Test on Pale House Mosquito (*Culex pipiens*) Larvae 200 ml of 10 ppm solution of each compound of the invention was placed in a tall dish of 9 cm in diameter and 6 cm in height. Then, 10 of the last instar larvae of Pale House Mosquitos were released in the dish. The tall dish was placed in a thermostatic chamber kept at 25° C., and the number of the mosquitos killed were determined after 96 hours. The mortalities were determined as in Test Example 3.

The results are shown in Table 7.
The above tests were repeated twice for each compound.

TEST EXAMPLE 5

Contact Insecticidal Test on Diamondback Moth (*Plutella xylostella*)

A leaf of cabbage was immersed in an aqueous emulsion containing 1000 ppm of each compound according to the present invention for about 10 seconds, and then air-dried. The leaf thus treated was placed in a dish, into which 10 second instar diamondback moth larvae were released. The dish was fitted with a cap provided with some pores and then placed in a thermostatic chamber kept at 25° C. The mortality of the diamondback moth after 96 hours was determined in the same manner as in Test Example 3. The results thereof are shown in Table 7.

TEST EXAMPLE 6

Contact Insecticidal Test on 28-Spotted Lady Beetle (*Henosepilachna vigintioctopunctata*)

A piece of potato was immersed in an aqueous emulsion containing 1000 ppm of a compound according to the present invention and then air-dried. The potato thus treated was placed in a laboratory dish, into which 10 second instar 28-spotted lady beetle larvae were released. The dish was then fitted with a cap provided with pores and then placed in a thermostatic chamber kept at 25° C. The number of the larvae killed was checked after 96 hours and the mortality thereof was determined in the same manner as Test Example 3.

The test results are shown in Table 7.

TEST EXAMPLE 7

Acaricidal Test on Kanzawa Spider Mite (*T. Kanzawai*)

A leaf of kidney bean was cut into a round piece of 1.5 cm in diameter by a leaf punch, and then placed on the moistened filter paper put on a styrol cup of 7 cm in diameter. Each piece of the leaf was inoculated with 10 Kanzawa Spider Mite nymph. Half a day after the inoculation, 2 ml of an aqueous emulsion containing 1000 ppm of the active substance with a spreader was applied to each styrol cup by means of a rotary spray tower. The number of the nymph killed was checked after 96 hours and the mortality of the nymph was determined. The results are shown in Table 7.

TEST EXAMPLE 8

Nematicidal Test on Root-knot Nematode (Meloidogyne spp.)

Soil contaminated with root-knot nematode was placed in a styrol cup of 8 cm in diameter. A liquid containing 1000 ppm of an active substance was prepared by diluting an emulsifiable concentrate according to the present invention with water and then a spreader was added thereto. The soil, contaminated with nematode and placed in the cup as described above, was drenched with 50 ml of the resulting liquid. After 48 hours, a tomato seedling as an indicator was transplanted into the soil thus treated. 30 days after the transplantation, the roots of the tomato were washed with water and the root-knot parasitism was checked by observation. The results are shown in Table 7.

Rating of Root-Knot Parasitism

0 . . . no root-knot observed at all.
1 . . . a few root-knots observed.
2 . . . a medium number of root-knot observed.
3 . . . many root-knots observed.
4 . . . considerably many root-knots observed.

TEST EXAMPLE 9

Insecticidal Test on Green Rice Leafhopper (*Nilaparvata lugens*)

Stems and leaves of paddy were immersed into 1000 ppm emulsion of each compound of the present invention for 10 seconds, and then the stems and leaves were placed into a glass cylinder. After the adults of green rice leafhopper, which would show the resistance to organic phosphorus type insecticides were released, the glass cylinder was covered with a lid having some pores and placed in a thermostatic chamber at 25° C. After 96 hours, the mortality was determined. The results are shown in Table 7.

TABLE 7
Results on insecticidal, miticidal, nematicidal test results

| Compound No. | House Fly (Musca domestica) (1000 ppm) | Pale House Mosquito (Culex pipiens) (10 ppm) | Diamondback Moth (Plutella xylostella) (1000 ppm) | 28-spotted Lady Beetle (Henosepilachna vigintioctopunctata) (1000 ppm) | Kanzawa Spider Mite (T. Kanzawai) (1000 ppm) | Root-knot Nematode (Meloidogyne spp.) (1000 ppm) | Green Rice Leafhopper (Nilaparvata lugen) (1000 ppm) |
|---|---|---|---|---|---|---|---|
| 1.11 | 100 | 90 | 90 | 100 | 100 | 0 | 75 |
| 1.12 | 60 | 95 | 70 | 65 | 100 | 1 | 100 |
| 1.16 | 100 | 100 | 100 | 50 | 100 | 0 | 75 |
| 1.17 | 100 | 85 | 70 | 100 | 90 | 1 | 100 |
| 1.19 | 100 | 95 | 95 | 100 | 100 | 0 | 95 |
| 1.20 | 85 | 60 | 100 | 100 | 100 | 1 | 100 |
| 1.22 | 95 | 85 | 90 | 100 | 75 | 1 | 75 |
| 1.23 | 100 | 45 | 90 | 90 | 100 | 1 | 100 |
| 1.24 | 100 | 90 | 95 | 100 | 100 | 0 | 80 |
| 1.29 | 100 | 95 | 60 | 100 | 100 | 1 | 65 |
| 1.37 | 50 | 60 | 80 | 100 | 100 | 1 | 90 |
| 1.38 | 80 | 80 | 85 | 55 | 100 | 0 | 60 |
| 1.39 | 100 | 100 | 100 | 100 | 100 | 1 | 95 |
| 1.46 | 80 | 95 | 45 | 70 | 100 | 1 | 85 |
| 1.47 | 100 | 90 | 55 | 60 | 100 | 1 | 65 |
| 1.72 | 50 | 70 | 100 | 100 | 100 | 0 | 100 |
| 1.73 | 100 | 80 | 100 | 100 | 100 | 1 | 100 |
| 1.75 | 100 | 100 | 100 | 100 | 100 | 1 | 100 |
| 1.76 | 70 | 90 | 100 | 100 | 80 | 1 | 70 |
| 1.78 | 80 | 85 | 95 | 100 | 100 | 0 | 100 |
| 1.79 | 100 | 100 | 100 | 80 | 100 | 1 | 100 |
| 1.80 | 100 | 100 | 95 | 100 | 100 | 1 | 100 |
| 1.81 | 100 | 95 | 100 | 70 | 100 | 1 | 95 |
| 1.84 | 70 | 60 | 80 | 100 | 100 | 1 | 100 |
| 1.86 | 100 | 70 | 100 | 70 | 100 | 1 | 100 |
| 1.87 | 100 | 50 | 75 | 85 | 100 | 1 | 80 |
| 1.88 | 95 | 90 | 100 | 100 | 100 | 0 | 80 |
| 2.1 | 100 | 100 | — | — | — | — | — |
| 2.3 | — | 100 | — | — | — | — | — |
| 2.5 | — | 100 | — | — | — | — | — |
| 2.10 | — | 100 | — | — | — | — | — |
| 2.11 | — | 100 | — | — | — | — | — |
| 2.12 | — | — | — | — | — | 0 | — |
| 2.27 | — | 100 | — | — | — | 0 | — |
| 2.28 | — | 100 | — | — | — | 0 | — |
| 2.29 | — | — | — | — | — | 0 | — |
| 2.31 | — | — | — | — | — | 0 | — |
| 2.34 | — | — | — | — | — | 0 | — |
| 2.35 | — | 100 | — | — | — | 0 | — |
| 2.36 | — | 100 | — | — | — | 0 | — |
| 2.55 | — | 100 | — | — | — | 0 | — |
| 2.57 | — | 100 | — | — | — | 0 | — |
| 2.62 | — | 100 | — | — | — | — | — |
| 2.69 | — | 100 | — | — | 100 | 0 | — |
| 2.71 | 100 | 100 | — | — | 100 | 0 | — |
| 2.72 | 100 | 100 | — | — | — | 0 | — |
| 2.73 | — | 100 | — | — | — | 0 | — |
| 2.74 | — | — | — | — | — | 0 | — |

TABLE 7-continued

Results on insecticidal, miticidal, nematicidal test results

| Compound No. | House Fly (Musca domestica) (1000 ppm) | Pale House Mosquito (Culex pipiens) (10 ppm) | Diamondback Moth (Plutella xylostella) (1000 ppm) | 28-spotted Lady Beetle (Henosepilachna vigintioctopunctata) (1000 ppm) | Kanzawa Spider Mite (T. Kanzawai) (1000 ppm) | Root-knot Nematode (Meloidogyne spp.) (1000 ppm) | Green Rice Leafhopper (Nilaparvata lugen) (1000 ppm) |
|---|---|---|---|---|---|---|---|
| 2.89 | 100 | — | — | — | — | 0 | — |
| 2.91 | — | 100 | — | — | 100 | 0 | — |
| 2.94 | — | 100 | — | — | — | 0 | — |
| 3.2 | 100 | 100 | 100 | 100 | 100 | 0 | — |
| 3.3 | 100 | 100 | — | 100 | 100 | 0 | — |
| 3.5 | — | 100 | — | — | 100 | 0 | — |
| 3.8 | 100 | 100 | 100 | 100 | 100 | 1 | 100 |
| 4.6 | 95 | 100 | 100 | 100 | 65 | 1 | 50 |
| 4.14 | 100 | 100 | 100 | 100 | 100 | 1 | 100 |
| 4.56 | 100 | 80 | 90 | 90 | 100 | 1 | 100 |
| 4.57 | — | — | 100 | 100 | 100 | 1 | 50 |
| 4.59 | 60 | 40 | 60 | 90 | 70 | 0 | 55 |
| 4.67 | 100 | 100 | 100 | 100 | 100 | 0 | — |
| 4.88 | 100 | 100 | 70 | 90 | 100 | 0 | — |
| 4.89 | 100 | 100 | 100 | 100 | 100 | 0 | — |
| 4.90 | — | 100 | 50 | 100 | 100 | 0 | — |
| 4.91 | — | 100 | 45 | 100 | 100 | 0 | — |

What we claim is:

1. A compound of the formula I:

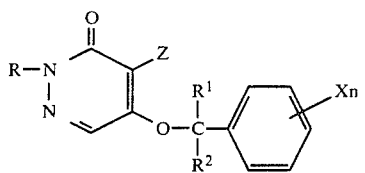

wherein, R denotes an $C_1$ to $C_6$ alkyl, $R^1$ and $R^2$ denote each independently hydrogen or a $C_1$ to $C_6$ alkyl, X denotes hydrogen, a $C_1$ to $C_6$ alkyl, a halogen, a $C_1$ to $C_6$ alkoxy, a $C_1$ to $C_6$ haloalkyl, a $C_1$ to $C_6$ haloalkoxy, $C_5$ to $C_6$ cycloalkyl, trimethylsilyl ($—Si(CH_3)_3$),

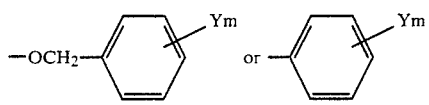

(wherein Y denotes hydrogen, a halogen, a $C_1$ to $C_6$ alkyl, a $C_1$ to $C_6$ alkoxy, a $C_1$ to $C_6$ haloalkyl, a $C_1$ to $C_6$ haloalkoxy or a cycloalkyl, and m is an integer of 1 to 5), n is an integer of 1 to 5, and Z denotes a halogen; said X being the same or different when n is 2 or more, the alkyls and the alkyl moieties contained in the groups being straight or branched, and the halogen itself or the halogen contained in the groups being selected from fluorine, chlorine, bromine or iodine or a mixture thereof.

2. A compound according to claim 1, in which the compound is represented by the formula IA:

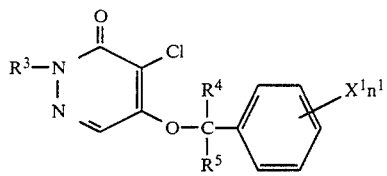

wherein, $R^3$ denotes a $C_1$ to $C_6$ alkyl, $R^4$ denotes a $C_1$ to $C_6$ alkyl; $R^5$ denotes hydrogen or a $C_1$ to $C_6$ alkyl; $X^1$ denotes hydrogen, a $C_1$ to $C_6$ alkyl, a $C_1$ to $C_6$ alkoxy, a $C_1$ to $C_6$ haloalkyl, a $C_1$ to $C_6$ haloalkoxy, a halogen or a $C_5$ to $C_6$ cycloalkyl, and $n^1$ is an integer of 1 to 5; said $X^1$ being the same or different when n is 2 to 5, and the alkyls and the alkyl moieties contained in the groups being straight or branched.

3. A compound according to claim 1, in which the compound is represented by the formula IB:

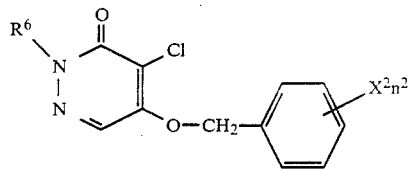

wherein, $R^6$ denotes an alkyl having 1 to 6 carbon atoms; $X^2$ denotes hydrogen, a halogen, a $C_1$ to $C_6$ alkyl, a $C_1$ to $C_6$ alkoxy or a $C_1$ to $C_6$ haloalkyoxy; and $n^2$ is an integer of 1 to 3; said $X^2$ being the same or different when $n^2$ is 2 or 3 and the alkyls and the alkyl moieties contained in the groups being straight or branched.

4. A compound according to claim 1, in which the compound is represented by the formula IC:

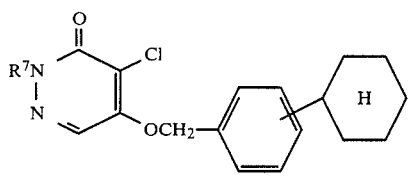

wherein, $R^7$ denotes a straight or branched alkyl.

5. A compound according to claim 1, in which the compound is represented by the formula ID:

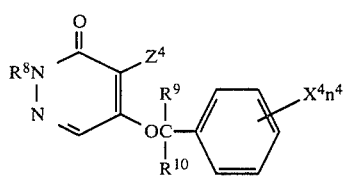

wherein, $R^8$ denotes a $C_1$ to $C_6$ alkyl; $R^9$ and $R^{10}$ denote each independently hydrogen or a $C_1$ to $C_6$ alkyl; $X^4$ denotes hydrogen, a $C_1$ to $C_6$ alkyl, a halogen, a $C_1$ to $C_6$ cycloalkyl, trimethylsilyl,

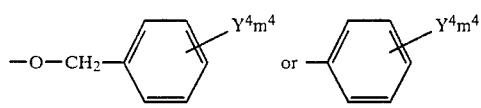

(wherein $Y^4$ denotes hydrogen, a halogen, a $C_1$ to $C_6$ alkyl, a $C_1$ to $C_6$ alkoxy, a $C_1$ to $C_6$ haloalkyl, a $C_1$ to $C_6$ haloalkoxy or a $C_5$ to $C_6$ cycloalkyl and $m^4$ is an integer of 1 to 5, said $Y^4$ being the same or different when $m^4$ is an integer of 2 to 5); $n^4$ is an integer of 1 to 3; and $Z^4$ is a halogen; said $X^4$ being the same or different when $n^4$ is 2 or 3 and the alkyls and the alkyl moieties contained in the groups being straight or branched.

6. A compound of the formula I:

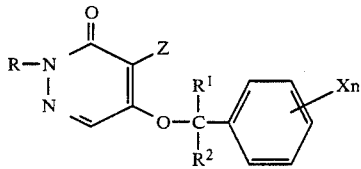

wherein R is $t-C_4H_9$, Z is Cl, $R^1$ is H, $R^2$ is H or $CH_3$, X is, at 4-position, $CH_3$, $t-C_4H_9$, F,

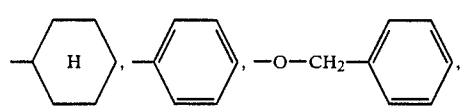

or $—Si(CH_3)_3$, and n is 1.

7. A process for preparing a compound of the formula I:

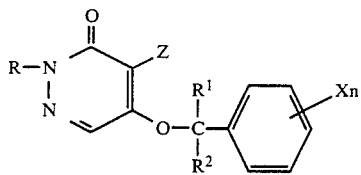

(I)

wherein, R denotes a $C_1$ to $C_6$ alkyl, $R^1$ and $R^2$ denote each independently hydrogen or a $C_1$ to $C_6$ alkyl, X denotes hydrogen, a $C_1$ to $C_6$ alkyl, a halogen, a $C_1$ to $C_6$ alkoxy, a $C_1$ to $C_6$ haloalkyl, a $C_1$ to $C_6$ haloalkoxy, a cycloalkyl, trimethylsilyl ($—Si(CH_3)_3$),

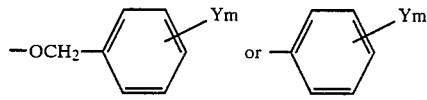

(wherein Y denotes hydrogen, a halogen, a $C_1$ to $C_6$ alkyl, a $C_1$ to $C_6$ alkoxy, a $C_1$ to $C_6$ haloalkyl, a $C_1$ to $C_6$ haloalkoxy or a cycloalkyl, and m is an integer of 1 to 5), n is an integer of 1 to 5, and Z denotes a halogen; said X being the same or different when n is 2 or more, and the alkyls and the alkyl moieties contained in the groups being straight or branched, by reacting a compound of the formula II:

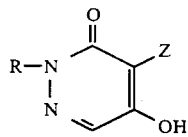

(II)

(wherein R and Z are as defined in the above) with a compound of the formula III:

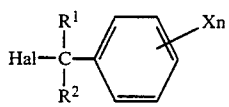

(III)

(wherein $R^1$, $R^2$, X and n are as defined in the above and Hal denotes a halogen atom).

8. A process according to claim 7, wherein the reaction is carried out in an inert solvent in the presence of a hydrogen halide-absorbing agent.

9. A process according to claim 7, wherein the reaction is carried out in the presence of a hydrogen-absorbing agent selected from sodium carbonate, potassium carbonate and triethylamine at a temperature of from room temperature up to the boiling point of the solvent employed.

10. A agricultural and horticultural fungicidal, insecticidal, acaricidal, nematocidal composition containing as an active ingredient an effective amount of a compound of the formula I:

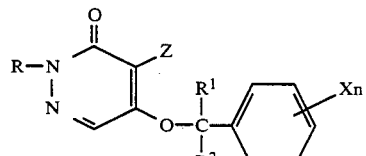

(I)

wherein, R denotes a $C_1$ to $C_6$ alkyl, $R^1$ and $R^2$ denote each independently hydrogen or a $C_1$ to $C_6$ alkyl, X denotes hydrogen, a $C_1$ to $C_6$ alkyl, a halogen, a $C_1$ to $C_6$ alkoxy, a $C_1$ to $C_6$ haloalkyl, a $C_1$ to $C_6$ haloalkoxy, a $C_1$ to $C_6$ cycloalkyl, trimethylsilyl ($—Si(CH_3)_3$),

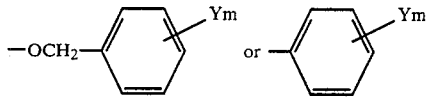

(wherein Y denotes hydrogen, a halogen, a $C_1$ to $C_6$ alkyl, a $C_1$ to $C_6$ alkoxy, a $C_1$ to $C_6$ haloalkyl, a $C_1$ to $C_6$ haloalkoxy or a $C_5$ to $C_6$ cycloalkyl, and m is an integer of 1 to 5), n is an integer of 1 to 5, and Z denotes a halogen; said X being the same or different when n is 2 or more, and the alkyls and the alkyl moieties contained in the groups being straight or branched, and a carrier therefor.

11. A composition according to claim 10, wherein R is t-$C_4H_9$, Z is C, $R^1$ is H, $R^2$ is H or $CH_3$, X is, at 4-position, $CH_3$, t-$C_4H_9$, F,

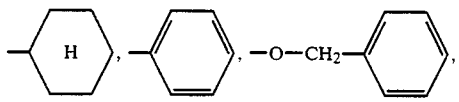

or $—Si(CH_3)_3$, and n is 1.

12. A method for fungicidal, insecticidal, acaricidal, nematocidal treatment in the agricultural and horticultural field with an effective amount of a compound of the formula (I):

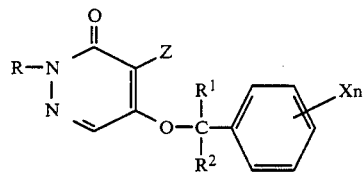

(I)

wherein, R denotes a $C_1$ to $C_6$ alkyl, $R^1$ and $R^2$ denote each independently hydrogen or a $C_1$ to $C_6$ alkyl, X denotes hydrogen, a $C_1$ to $C_6$ alkyl, a halogen, a $C_1$ to $C_6$ alkoxy, a $C_1$ to $C_6$ haloalkyl, a $C_1$ to $C_6$ haloalkoxy, a $C_5$ to $C_6$ cycloalkyl, trimethylsilyl ($—Si(CH_3)_3$),

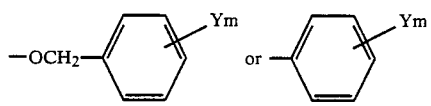

(wherein Y denotes hydrogen, a halogen, a $C_1$ to $C_6$ alkyl, a $C_1$ to $C_6$ alkoxy, a $C_1$ to $C_6$ haloalkyl, a $C_1$ to $C_6$ haloalkoxy or a $C_5$ to $C_6$ cycloalkyl, and m is an integer of 1 to 5), n is an integer of 1 to 5, and Z denotes a halogen; said X being the same or different when n is 2 or more, and the alkyls and alkyl moieties contained in the groups being straight or branched.

13. A process according to claim 8, wherein the reaction is carried out in the presence of a hydrogen-absorbing agent selected from sodium carbonate, potassium carbonate and triethylamine at a temperature of from room temperature up to the boiling point of the solvent employed.

14. The compound of claim 1 of the formula:

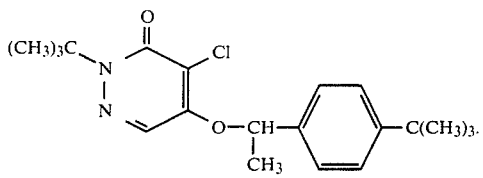

15. The compound of claim 1 of the formula:

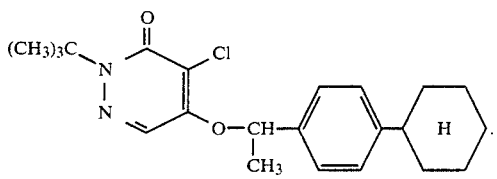

16. The compound of claim 1 of the formula:

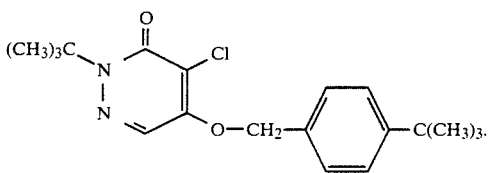

17. The compound of claim 1 of the formula:

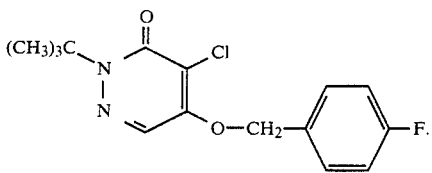

18. The compound of claim 1 of the formula:

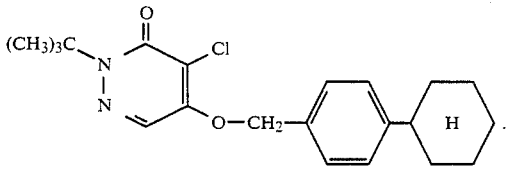

19. The compound of claim 1 of the formula:

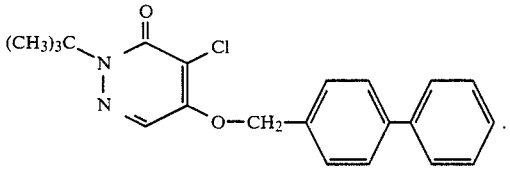

20. The compound of claim 1 of the formula:

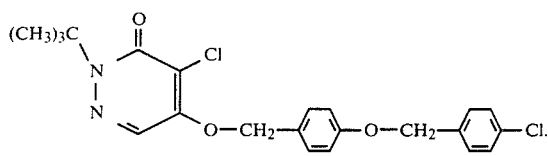

21. The compound of claim 1 of the formula:

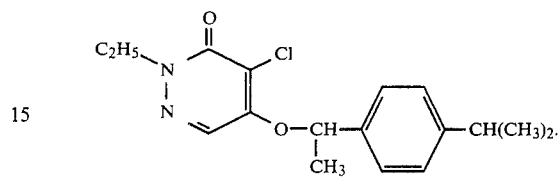

22. The compound of claim 1 of the formula:

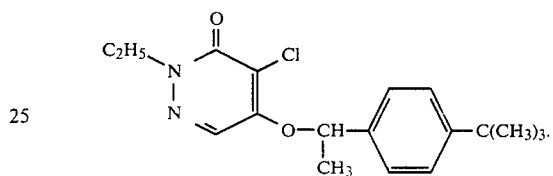

23. The compound of claim 1 of the formula:

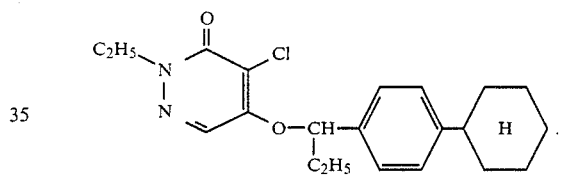

24. The compound of claim 1 of the formula:

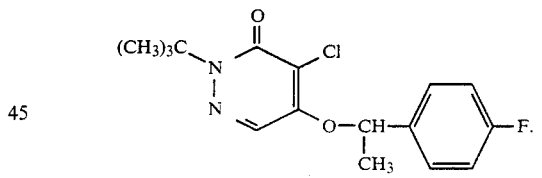

25. The compound of claim 1 of the formula:

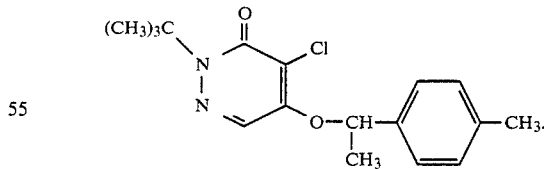

26. The compound of claim 1 of the formula:

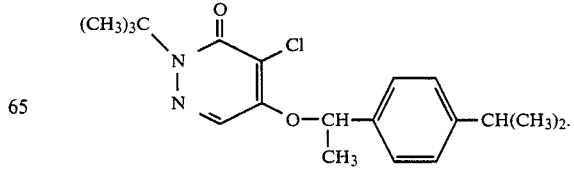

27. The compound of claim 1 of the formula:
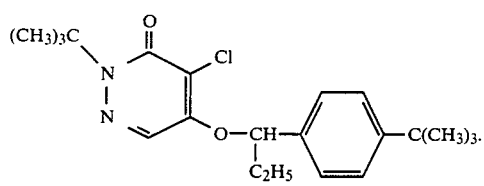
28. The compound of claim 1 of the formula:
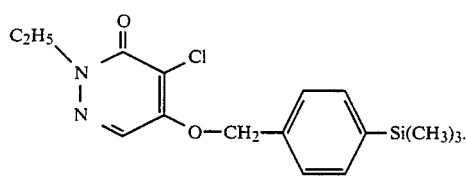
29. The compound of claim 1 of the formula:
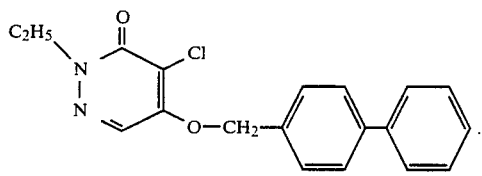
30. The compound of claim 1 of the formula:
31. The compound of claim 1 of the formula:
32. The compound of claim 1 of the formula:
33. A compound according to claim 1, wherein Z is Cl or Br.
* * * * *

UNITED STATES PATENT OFFICE
CERTIFICATE OF CORRECTION

Patent No. 4,571,397                Dated  February 18, 1986

Inventor(s) Taniguchi et al

It is certified that error appears in the above-identified patent and that said Letters Patent are hereby corrected as shown below:

Column 34, Line 21, in Claim 11, for "Z is C,", please read --Z is Cl,--.

Signed and Sealed this

Twenty-fourth Day of June 1986

[SEAL]

Attest:

DONALD J. QUIGG

Attesting Officer     Commissioner of Patents and Trademarks